US012759954B2

(12) United States Patent
Wendlinger

(10) Patent No.: US 12,759,954 B2
(45) Date of Patent: Oct. 13, 2026

(54) COMPOSITION COMPRISING AN IODOFLUOROCARBON COMPOUND

(71) Applicant: ARKEMA FRANCE, Colombes (FR)

(72) Inventor: Laurent Wendlinger, Pierre-Benite Cedex (FR)

(73) Assignee: ARKEMA FRANCE, Puteaux (FR)

( * ) Notice: Subject to any disclaimer, the term of this patent is extended or adjusted under 35 U.S.C. 154(b) by 1093 days.

(21) Appl. No.: 17/904,382

(22) PCT Filed: Feb. 17, 2021

(86) PCT No.: PCT/FR2021/050284

§ 371 (c)(1),
(2) Date: Aug. 17, 2022

(87) PCT Pub. No.: WO2021/165618

PCT Pub. Date: Aug. 26, 2021

(65) Prior Publication Data

US 2023/0114828 A1 Apr. 13, 2023

(30) Foreign Application Priority Data

Feb. 19, 2020 (FR) .................................... 2001621

(51) Int. Cl.
*C07C 19/16* (2006.01)
*C07C 21/17* (2006.01)
*C07C 21/18* (2006.01)

(52) U.S. Cl.
CPC .............. *C07C 19/16* (2013.01); *C07C 21/17* (2013.01); *C07C 21/18* (2013.01)

(58) Field of Classification Search
CPC ......... C07C 19/16; C07C 21/17; C07C 21/18; C11D 7/30; C11D 7/505; C11D 7/5068; C11D 7/5018
See application file for complete search history.

(56) References Cited

U.S. PATENT DOCUMENTS

2017/0178923 A1 6/2017 Surla et al.

FOREIGN PATENT DOCUMENTS

| | | | |
|---|---|---|---|
| CN | 107112186 | A | 8/2017 |
| CN | 107176902 | A | 9/2017 |
| CN | 108675914 | A | 10/2018 |
| FR | 2001617 | A1 | 9/1969 |
| FR | 2001619 | A1 | 9/1969 |
| FR | 2001620 | A1 | 9/1969 |
| GB | 1228504 | A | 4/1971 |
| GB | 1231562 | A | 5/1971 |
| GB | 1250077 | A | 10/1971 |
| JP | H10231261 | A | 9/1998 |
| WO | 2006063241 | A2 | 6/2006 |
| WO | 2006112881 | A1 | 10/2006 |
| WO | 2009019219 | A2 | 2/2009 |
| WO | 2016036739 | A1 | 3/2016 |
| WO | 2020031801 | A1 | 2/2020 |

OTHER PUBLICATIONS

Yulong Shen et al., "Cataloging in Publication (CIP) Data for Books Green Chemistry", China Environmental Publishing House, 7th printing, 3rd edition, Apr. 2016, pp. 186-187, with English translation.

Jon Nimitz, "Status of Development of Fluoroiodocarbon (FIC) Solvents as Environmentally Safe, Nonflammable, Drop-in Replacements for Chlorinated Solvents", Environmental Technology & Education Center (ETEC), 21st Mr. Clean Conference, Apr. 1996, 13 pages.

ISA/EP; International Search Report and Written Opinion for International Patent Application No. PCT/FR2021/050284 dated Aug. 6, 2021, 22 pages.

Mao, Aiqin, et al., "Effects of acid treatment on activated carbon used as a support for Rb and K catalyst for CFI synthesis and its mechanism", Journal of Fluorine Chemistry, Elsevier, vol. 132, No. 8, May 30, 2011, 6 pages.

Hauptschein, Murray, et al., "Notes—Thermal Reaction of 1, 1-Difluoroethylene with Iodine", The Journal of Organic Chemistry, vol. 23, No. 2, Feb. 1, 1958, 1 page.

*Primary Examiner* — Jafar F Parsa
(74) *Attorney, Agent, or Firm* — Rimon P.C.; Allyn B. Elliott

(57) ABSTRACT

A composition comprises at least 99.5% by weight of an iodofluorocarbon compound A and at most 0.5% by weight of a compound B selected from water, HF, HI, IF5, I2, O2, CO2, CO and nitrogen. The iodofluorocarbon compound A is of formula (I) (R1)(R2)C(I)(R3) or of formula (II) (R1)(R2)C═C(I)(R3); in which R1, R2 and R3 independently of one another are selected from the group consisting of H, F, I, a C1-C10 alkyl radical, a C3-C10 cycloalkyl radical, a C2-C10 alkenyl radical, a C3-C10 cycloalkenyl radical, and a C6-C10 aryl radical. All radicals are optionally substituted by a fluorine or iodine atom. At least one of the substituents R1, R2 or R3, is F or is a radical as defined above comprising at least one fluorine atom. The iodofluorocarbon compound A is not CF3I.

18 Claims, No Drawings

COMPOSITION COMPRISING AN IODOFLUOROCARBON COMPOUND

CROSS-REFERENCE TO RELATED APPLICATIONS

This application is a U.S. National Stage application of International Patent Application No. PCT/FR2021/050284, filed on Feb. 17, 2021, which claims the benefit of French Patent Application No. FR2001621, filed on Feb. 19, 2020.

TECHNICAL FIELD OF THE INVENTION

The present invention relates to a composition comprising an iodofluorocarbon compound. In particular, the present invention relates to a composition comprising an iodofluoroalkane compound. The present invention also relates to a composition comprising an iodofluoroolefin compound. The present invention also relates to the use of said composition as refrigerant, solvent, foam blowing agent, aerosol propellant, fire extinguisher, desiccant, in order to eliminate the water adsorbed on the surface of solid parts, and degreasing and cleaning agent for various surfaces, in particular as precision cleaning agent.

TECHNOLOGICAL BACKGROUND OF THE INVENTION

Considering the reactivity of their iodine atom, the iodofluoro compounds are important synthetic intermediates for the manufacture of pharmaceutical products, phytosanitary products, extinguishers and products to treating various substrates, notably substrates intended for applications in electronics.

The iodofluoro compounds also find applications in the field of refrigeration or in air-conditioning devices. Compositions are known from WO 2006/112881 that comprise $CF_3I$ and HFC-152A and that are intended to be used in refrigerant compositions, in refrigeration systems, in compositions based on blowing agents, in aerosol propellants and others.

The applications in these various fields require the use of particularly pure compounds. The objective of the present invention is to provide compositions suitable for use in these applications.

SUMMARY OF THE INVENTION

According to a first aspect, the present invention relates to a composition comprising at least 99.5% by weight of an iodofluorocarbon compound A and at most 0.5% by weight of at least one compound B chosen from water, HF, HI, $IF_5$, $I_2$, $O_2$, $CO_2$, CO and nitrogen or a mixture thereof; said iodofluorocarbon compound A being of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with at least one fluorine or iodine atom, a $C_3$-$C_{10}$ cycloalkyl radical optionally substituted with at least one fluorine or iodine atom, a $C_2$-$C_{10}$ alkenyl radical optionally substituted with at least one fluorine or iodine atom, a $C_3$-$C_{10}$ cycloalkenyl radical optionally substituted with at least one fluorine or iodine atom, and a $C_6$-$C_{10}$ aryl radical optionally substituted with at least one fluorine or iodine atom; on condition that at least one of the substituents $R^1$, $R^2$ or $R^3$ is F or is a radical as defined above comprising at least one fluorine atom and on condition that the iodofluorocarbon compound A is not $CF_3I$.

According to a preferred embodiment, said composition comprises at least 99.9% by weight, preferably at least 99.95% by weight, of said compound A and at most 0.1% by weight, preferably at most 0.05% by weight, of said at least one compound B.

According to a preferred embodiment, said composition comprises at least 99.9% by weight, preferably at least 99.95% by weight, of said compound A and at most 1000 ppm of water, preferably at most 100 ppm of water, in particular at most 10 ppm of water.

In the present invention, the term ppm refers to ppm by weight.

According to a preferred embodiment, said composition comprises at least 99.9% by weight, preferably at least 99.95% by weight, of said compound A and at most 1000 ppm of HI, preferably at most 100 ppm of HI, in particular at most 10 ppm of HI.

According to a preferred embodiment, said composition comprises at least 99.9% by weight, preferably at least 99.95% by weight, of said compound A and at most 1000 ppm of HF, preferably at most 100 ppm of HF, in particular at most 10 ppm of HF.

According to a preferred embodiment, said composition comprises at least 99.9% by weight, preferably at least 99.95% by weight, of said compound A and at most 1000 ppm of $IF_5$, preferably at most 100 ppm of $IF_5$, in particular at most 10 ppm of $IF_5$.

According to a preferred embodiment, said composition comprises at least 99.9% by weight, preferably at least 99.95% by weight, of said compound A and at most 1000 ppm of $I_2$, preferably at most 100 ppm of $I_2$, in particular at most 10 ppm of $I_2$.

According to a preferred embodiment, said composition comprises at least 99.9% by weight, preferably at least 99.95% by weight, of said compound A and at most 1000 ppm of $O_2$, preferably at most 100 ppm of $O_2$, in particular at most 10 ppm of $O_2$.

According to a preferred embodiment, said composition comprises at least 99.9% by weight, preferably at least 99.95% by weight, of said compound A and at most 1000 ppm of $CO_2$, preferably at most 100 ppm of $CO_2$, in particular at most 10 ppm of $CO_2$.

According to a preferred embodiment, said composition comprises at least 99.9% by weight, preferably at least 99.95% by weight, of said compound A and at most 1000 ppm of CO, preferably at most 100 ppm of CO, in particular at most 10 ppm of CO.

According to a preferred embodiment, said composition comprises at least 99.9% by weight, preferably at least 99.95% by weight, of said compound A and at most 1000 ppm of nitrogen, preferably at most 100 ppm of nitrogen, in particular at most 10 ppm of nitrogen.

According to a preferred embodiment, said compound A is of formula (I) or (II), wherein $R^1$, $R^2$ and $R^3$ are, independently of one another, selected from the group consisting of H, F, I, a $C_1$-$C_5$ perfluoroalkyl radical, a $C_5$-$C_{10}$ perfluorocycloalkyl radical, a $C_2$-$C_5$perfluoroalkenyl radical, a $C_5$-$C_{10}$ perfluorocycloalkenyl radical, a $C_6$-$C_{10}$ perfluoroaryl radical; on condition that at least one of the substituents $R^1$, $R^2$ or $R^3$ is F or is a radical as defined here comprising at least one fluorine atom; and on condition that the iodofluorocarbon compound A is not $CF_3I$.

According to a preferred embodiment, said compound A is of formula (I) or (II), wherein $R^1$, $R^2$ and $R^3$ are, independently of one another, selected from the group consisting of H, F or Y$^1$—[—C(Y$^2$)(Y$^3$)—]$_n$— wherein Y$^1$, Y$^2$, and Y$^3$ are, independently of one another and independently for each unit n, selected from the group consisting of H, I and F; and n is an integer from 1 to 5; on condition that at least one of the substituents R$^1$, R$^2$, R$^3$, Y$^1$, Y$^2$ or Y$^3$ is a fluorine atom and on condition that the iodofluorocarbon compound A is not CF$_3$I.

According to a preferred embodiment, said compound A is selected from the group consisting of CH$_2$FI, CHF$_2$I, CH$_2$F—CH$_2$I, CHFI—CH$_3$, CFI═CH$_2$, cis-CHF═CHI, trans-CHF═CHI, CHF$_2$—CH$_2$I, CF$_2$I—CH$_3$, CF$_3$—CH$_2$I, CF$_2$═CHI, CH$_2$F—CHFI, cis-CFI═CHF, trans-CFI═CHF, CHF$_2$—CHFI, CF$_2$I—CH$_2$F, CF$_3$—CHFI, CF$_2$═CFI, CHF$_2$—CF$_2$I, CF$_2$I—CF$_3$, CH$_3$—CHF—CH$_2$I, CH$_3$—CFI—CH$_3$, CH$_3$—CF$_2$—CH$_2$I, CH$_2$═CF—CH$_2$I, cis-CH$_3$—CF═CHI, trans-CH$_3$—CF═CHI, CH$_3$—CH$_2$—CHFI, CH$_3$—CHI—CH$_2$F, CH$_2$═CH—CHFI, cis-CH$_3$—CI═CHF, trans-CH$_3$—CI═CHF, cis-CH$_3$—CH═CFI, trans-CH$_3$—CH═CFI, CH$_2$F—CH$_2$—CH$_2$I, cis-CHF═CH—CH$_2$I, trans-CHF═CH—CH$_2$I, CH$_2$F—CI═CH$_2$, cis-CH$_2$F—CH═CHI, trans-CH$_2$F—CH═CHI, CH$_3$—CHF—CHFI, CH$_3$—CFI—CH$_2$F, CH$_3$—CF$_2$—CHFI, CH$_2$═CF—CHFI, cis-CH$_3$—CF═CFI, trans-CH$_3$—CF═CFI, CH$_2$F—CHF—CH$_2$I, CH$_2$F—CF$_2$—CH$_2$I, cis-CHF═CF—CH$_2$I, trans-CHF═CF—CH$_2$I, cis-CH$_2$F—CF═CHI, trans-CH$_2$F—CF═CHI, CH$_3$—CH$_2$—CF$_2$I, CH$_3$—CHI—CHF$_2$, CH$_2$═CH—CF$_2$I, CH$_3$—CI═CF$_2$, CH$_2$F—CH$_2$—CHFI, CH$_2$F—CHI—CH$_2$F, cis-CHF═CH—CHFI, trans-CHF═CH—CHFI, cis-CH$_2$F—CI═CHF, trans-CH$_2$F—CI═CHF, cis-CH$_2$F—CH═CFI, trans-CH$_2$F—CH═CFI, CHF$_2$—CH$_2$—CH$_2$I, CF$_2$═CH—CH$_2$I, CHF$_2$—CI═CH$_2$, cis-CHF$_2$—CH═CHI, trans-CHF$_2$—CH═CHI, CH$_3$—CHF—CF$_2$I, CH$_3$—CFI—CHF$_2$, CH$_3$—CF$_2$—CF$_2$I, CH$_2$═CF—CF$_2$I, CH$_2$F—CHF—CHFI, CH$_2$F—CFI—CH$_2$F, CH$_2$F—CF$_2$—CHFI, cis-CHF═CF—CHFI, trans-CHF═CF—CHFI, cis-CH$_2$F—CF═CFI, trans-CH$_2$F—CF═CFI, CHF$_2$—CHF—CH$_2$I, CHF$_2$—CF$_2$—CH$_2$I, CF$_2$═CF—CH$_2$I, cis-CHF$_2$—CF═CHI, trans-CHF$_2$—CF═CHI, CH$_2$F—CH$_2$—CF$_2$I, CH$_2$F—CHI—CHF$_2$, cis-CHF═CH—CF$_2$I, trans-CHF═CH—CF$_2$I, CH$_2$F—CI═CF$_2$, CHF$_2$—CH$_2$—CHFI, CF$_2$═CH—CHFI, cis-CHF$_2$—CI═CHF, trans-CHF$_2$—CI═CHF, cis-CHF$_2$—CH═CFI, trans-CHF$_2$—CH═CFI, CF$_3$—CH$_2$—CH$_2$I, CF$_3$—CHI—CH$_3$, CF$_3$—CI═CH$_2$, cis-CF$_3$—CH═CHI, trans-CF$_3$—CH═CHI, CH$_2$F—CHF—CF$_2$I, CH$_2$F—CFI—CHF$_2$, CH$_2$F—CF$_2$—CF$_2$I, cis-CHF═CF—CF$_2$I, trans-CHF═CF—CF$_2$I, CHF$_2$—CHF—CHFI, CHF$_2$—CF$_2$—CHFI, CF$_2$═CF—CHFI, cis-CHF$_2$—CF═CFI, trans-CHF$_2$—CF═CFI, CF$_3$—CHF—CH$_2$I, CF$_3$—CFI—CH$_3$, CF$_3$—CF$_2$—CH$_2$I, cis-CF$_3$—CF═CHI, trans-CF$_3$—CF═CHI, CHF$_2$—CH$_2$—CF$_2$I, CHF$_2$—CHI—CHF$_2$, CF$_2$═CH—CF$_2$I, CHF$_2$—CI═CF$_2$, CF$_3$—CH$_2$—CHFI, CF$_3$—CHI—CH$_2$F, cis-CF$_3$—CI═CHF, trans-CF$_3$—CI═CHF, cis-CF$_3$—CH═CFI, trans-CF$_3$—CH═CFI, CHF$_2$—CHF—CF$_2$I, CHF$_2$—CFI—CHF$_2$, CHF$_2$—CF$_2$—CF$_2$I, CF$_2$═CF—CF$_2$I, CF$_3$—CHF—CHFI, CF$_3$—CFI—CH$_2$F, CF$_3$—CF$_2$—CHFI, cis-CF$_3$—CF═CFI, trans-CF$_3$—CF═CFI, CF$_3$—CH$_2$—CF$_2$I, CF$_3$—CHI—CHF$_2$, CF$_3$—CHI—CF$_3$, CF$_3$—CI═CF$_2$, CF$_3$—CHF—CF$_2$I, CF$_3$—CFI—CHF$_2$, CF$_3$—CFI—CF$_3$, CF$_3$—CF$_2$—CF$_2$I.

According to a preferred embodiment, said compound A is selected from the group consisting of CHF$_2$I, CHF$_2$—CH$_2$I, CF$_2$I—CH$_3$, CF$_3$—CH$_2$I, CF$_2$═CHI, CHF$_2$—CHFI, CF$_2$I—CH$_2$F, CF$_3$—CHFI, CF$_2$═CFI, CHF$_2$—CF$_2$I, CF$_2$I—CF$_3$, CF$_3$—CH$_2$—CH$_2$I, CF$_3$—CHI—CH$_3$, CF$_3$—CI═CH$_2$, cis-CF$_3$—CH═CHI, trans-CF$_3$—CH═CHI, CF$_3$—CHF—CH$_2$I, CF$_3$—CFI—CH$_3$, CF$_3$—CF$_2$—CH$_2$I, cis-CF$_3$—CF═CHI, trans-CF$_3$—CF═CHI, CF$_3$—CH$_2$—CHFI, CF$_3$—CHI—CH$_2$F, cis-CF$_3$—CI═CHF, trans-CF$_3$—CI═CHF, cis-CF$_3$—CH═CFI, trans-CF$_3$—CH═CFI, CF$_3$—CHF—CHFI, CF$_3$—CFI—CH$_2$F, CF$_3$—CF$_2$—CHFI, cis-CF$_3$—CF═CFI, trans-CF$_3$—CF═CFI, CF$_3$—CHF—CF$_2$I, CF$_3$—CFI—CHF$_2$, CF$_3$—CFI—CF$_3$, CF$_3$—CF$_2$—CF$_2$I.

According to a preferred embodiment, said compound A is selected from the group consisting of CHFI$_2$, CF$_2$I$_2$, CFI$_2$—CH$_3$, CH$_2$F—CHI$_2$, CHFI—CH$_2$I, CHF$_2$—CHI$_2$, CF$_2$I—CH$_2$I, CFI$_2$—CH$_2$F, CHFI—CHFI, CF$_3$—CHI$_2$, CHF$_2$—CFI$_2$, CF$_2$I—CHFI, CF$_3$—CFI$_2$, CF$_2$I—CF$_2$I, CFI$_2$—CH$_2$—CH$_3$, CH$_2$F—CI$_2$—CH$_3$, CH$_2$F—CH$_2$—CHI$_2$, CHFI—CHI—CH$_3$, CHFI—CH$_2$—CH$_2$I, CH$_2$F—CHI—CH$_2$I, CHI$_2$—CHF—CH$_3$, CH$_2$I—CFI—CH$_3$, CH$_2$I—CHF—CH$_2$I, CFI$_2$—CH$_2$—CH$_2$F, CH$_2$F—CI$_2$—CH$_2$F, CHFI—CHI—CH$_2$F, CHFI—CH$_2$—CHFI, CHF$_2$—CI$_2$—CH$_3$, CHF$_2$—CH$_2$—CHI$_2$, CF$_2$I—CHI—CH$_3$, CF$_2$I—CH$_2$—CH$_2$I, CHF$_2$—CHI—CH$_2$I, CFI$_2$—CHF—CH$_3$, CH$_2$F—CHF—CHI$_2$, CHFI—CFI—CH$_3$, CHFI—CHF—CH$_2$I, CH$_2$F—CFI—CH$_2$I, CHI$_2$—CF$_2$—CH$_3$, CH$_2$I—CF$_2$—CH$_2$I, CHF$_2$—CI$_2$—CH$_2$F, CHF$_2$—CH$_2$—CFI$_2$, CF$_2$I—CHI—CH$_2$F, CF$_2$I—CH$_2$—CHFI, CHF$_2$—CHI—CHFI, CF$_3$—CI$_2$—CH$_3$, CF$_3$—CH$_2$—CHI$_2$, CF$_3$—CHI—CH$_2$I, CFI$_2$—CHF—CH$_2$F, CHFI—CFI—CH$_2$F, CHFI—CHF—CHFI, CHF$_2$—CHF—CHI$_2$, CF$_2$I—CFI—CH$_3$, CF$_2$I—CHF—CH$_2$I, CHF$_2$—CFI—CH$_2$I, CFI$_2$—CF$_2$—CH$_3$, CH$_2$F—CF$_2$—CHI$_2$, CHFI—CF$_2$—CH$_2$I, CHF$_2$—CI$_2$—CHF$_2$, CF$_2$I—CHI—CHF$_2$, CF$_2$I—CH$_2$—CF$_2$I, CF$_3$—CI$_2$—CH$_2$F, CF$_3$—CH$_2$—CFI$_2$, F$_3$—CHI—CHFI, CHF$_2$—CHF—CFI$_2$, CF$_2$I—CFI—CH$_2$F, CF$_2$I—CHF—CHFI, CHF$_2$—CFI—CHFI, CF$_3$—CHF—CHI$_2$, CF$_3$—CFI—CH$_2$I, CFI$_2$—CF$_2$—CH$_2$F, CHFI—CF$_2$—CHFI, CHF$_2$—CF$_2$—CHI$_2$, CF$_2$I—CF$_2$—CH$_2$I, CF$_3$—CI$_2$—CHF$_2$, CF$_3$—CHI—CF$_2$I, CF$_2$I—CFI—CHF$_2$, CF$_2$I—CHF—CF$_2$I, CF$_3$—CHF—CFI$_2$, CF$_3$—CFI—CHFI, CHF$_2$—CF$_2$—CFI$_2$, CF$_2$I—CF$_2$—CHFI, CF$_3$—CF$_2$—CHI$_2$, CF$_3$—CI$_2$—CF$_3$, CF$_3$—CFI—CF$_2$I, CF$_2$I—CF$_2$—CF$_2$I, CF$_3$—CF$_2$—CFI$_2$.

According to a preferred embodiment, said compound A is selected from the group consisting of CF$_2$I$_2$, CHF$_2$—CHI$_2$, CF$_2$I—CH$_2$I, CF$_3$—CHI$_2$, CF$_3$—CFI$_2$, CFI$_2$—CHF—CH$_3$, CH$_2$F—CHF—CHI$_2$, CHFI—CFI—CH$_3$, CHFI—CHF—CH$_2$I, CH$_2$F—CFI—CH$_2$I, CF$_3$—CI$_2$—CH$_3$, CF$_3$—CH$_2$—CHI$_2$, CF$_3$—CHI—CH$_2$I, CF$_3$—CI$_2$—CH$_2$F, CF$_3$—CH$_2$—CFI$_2$, CF$_3$—CHI—CHFI, CF$_3$—CHF—CHI$_2$, CF$_3$—CFI—CH$_2$I, CF$_3$—CI$_2$—CHF$_2$, CF$_3$—CHI—CF$_2$I, CF$_3$—CHF—CFI$_2$, CF$_3$—CFI—CHFI, CF$_3$—CI$_2$—CF$_3$, CF$_3$—CFI—CF$_2$I, CF$_2$I—CHFI.

According to a second aspect, the present invention relates to the use of a composition according to the present invention as a precision cleaning agent.

According to a third aspect, the present invention provides a storage device comprising a sealed container within which the composition according to the invention is contained.

DETAILED DESCRIPTION OF THE INVENTION

The present invention relates to a composition comprising an iodofluorocarbon compound A. Said composition comprises at least 99.5% by weight of said iodofluorocarbon compound A on the basis of the total weight of the composition, advantageously at least 99.6% by weight of said iodofluorocarbon compound A, preferably at least 99.7% by weight of said iodofluorocarbon compound A, more preferentially at least 99.8% by weight of said iodofluorocarbon compound A, in particular at least 99.9% by weight of said iodofluorocarbon compound A, more particularly at least 99.95% by weight of said iodofluorocarbon compound A on the basis of the total weight of the composition.

Advantageously, said iodofluorocarbon compound A is of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with at least one fluorine or iodine atom, a $C_3$-$C_{10}$ cycloalkyl radical optionally substituted with at least one fluorine or iodine atom, a $C_2$-$C_{10}$ alkenyl radical optionally substituted with at least one fluorine or iodine atom, a $C_3$-$C_{10}$ cycloalkenyl radical optionally substituted with at least one fluorine or iodine atom, and a $C_6$-$C_{10}$ aryl radical optionally substituted with at least one fluorine or iodine atom; on condition that at least one of the substituents $R^1$, $R^2$ or $R^3$ is F or is a radical as defined above comprising at least one fluorine atom.

Advantageously, said iodofluorocarbon compound A is of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with at least one fluorine or iodine atom, a $C_3$-$C_{10}$ cycloalkyl radical optionally substituted with at least one fluorine or iodine atom, a $C_2$-$C_{10}$ alkenyl radical optionally substituted with at least one fluorine or iodine atom, a $C_3$-$C_{10}$ cycloalkenyl radical optionally substituted with at least one fluorine or iodine atom, and a $C_6$-$C_{10}$ aryl radical optionally substituted with at least one fluorine or iodine atom; on condition that at least one of the substituents $R^1$, $R^2$ or $R^3$ is F or is a radical as defined above comprising at least one fluorine atom; and on condition that the iodofluorocarbon compound A is not $CF_3I$.

Alternatively, said iodofluorocarbon compound A is $CF_3I$.

The term "alkyl" denotes a monovalent radical resulting from a linear or branched alkane comprising the number of carbon atoms specified. The term "cycloalkyl" denotes a monovalent radical resulting from a cycloalkane comprising the number of carbon atoms specified. The term "alkenyl" denotes a monovalent radical comprising the number of carbon atoms specified and at least one carbon-carbon double bond. The term "cycloalkenyl" refers to a monovalent radical resulting from a cycloalkene comprising the number of carbon atoms specified and at least one carbon-carbon double bond in its cyclic part. The term "aryl" denotes a monovalent radical resulting from an arene comprising the number of carbon atoms specified. Preferably, said alkyl, cycloalkyl, alkenyl, cycloalkenyl or aryl radical is not substituted with functional groups other than fluorine or iodine. Said radical may nevertheless comprise several fluorine atoms on its carbon-based chain or several iodine atoms on its carbon-based chain. For example, said radical may contain from 1 to 10 fluorine atoms, preferably from 1 to 5 fluorine atoms. For example, said radical may contain from 1 to 3 iodine atoms, preferably one or two iodine atoms.

Advantageously, said iodofluorocarbon compound A is of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with 1 to 10 fluorine atoms and/or 1 to 3 iodine atoms, a $C_3$-$C_{10}$ cycloalkyl radical optionally substituted with 1 to 10 fluorine atoms and/or 1 to 3 iodine atoms, a $C_2$-$C_{10}$ alkenyl radical optionally substituted with 1 to 10 fluorine atoms and/or 1 to 3 iodine atoms, a $C_3$-$C_{10}$ cycloalkenyl radical optionally substituted with 1 to 10 fluorine atoms and/or 1 to 3 iodine atoms, and a $C_6$-$C_{10}$ aryl radical optionally substituted with 1 to 10 fluorine atoms and/or 1 to 3 iodine atoms; on condition that at least one of the substituents $R^1$, $R^2$ or $R^3$ is F or is a radical as defined above comprising at least one fluorine atom. More advantageously, said iodofluorocarbon compound A is of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with 1 to 10 fluorine atoms and/or 1 to 3 iodine atoms, a $C_3$-$C_{10}$ cycloalkyl radical optionally substituted with 1 to 10 fluorine atoms and/or 1 to 3 iodine atoms, a $C_2$-$C_{10}$ alkenyl radical optionally substituted with 1 to 10 fluorine atoms and/or 1 to 3 iodine atoms, a $C_3$-$C_{10}$ cycloalkenyl radical optionally substituted with 1 to 10 fluorine atoms and/or 1 to 3 iodine atoms, and a $C_6$-$C_{10}$ aryl radical optionally substituted with 1 to 10 fluorine atoms and/or 1 to 3 iodine atoms; on condition that at least one of the substituents $R^1$, $R^2$ or $R^3$ is F or is a radical as defined above comprising at least one fluorine atom; and on condition that the iodofluorocarbon compound A is not $CF_3I$.

Preferably, said iodofluorocarbon compound A is of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with 1 to 5 fluorine atoms and/or 1 to 2 iodine atoms, a $C_3$-$C_{10}$ cycloalkyl radical optionally substituted with 1 to 5 fluorine atoms and/or 1 to 2 iodine atoms, a $C_2$-$C_{10}$ alkenyl radical optionally substituted with 1 to 5 fluorine atoms and/or 1 to 2 iodine atoms, a $C_3$-$C_{10}$ cycloalkenyl radical optionally substituted with 1 to 5 fluorine atoms and/or 1 to 2 iodine atoms, and a $C_6$-$C_{10}$ aryl radical optionally substituted with 1 to 5 fluorine atoms and/or 1 to 2 iodine atoms; on condition that at least one of the substituents $R^1$, $R^2$ or $R^3$ is F or is a radical as defined above comprising at least one fluorine atom. Alternatively, said iodofluorocarbon compound A is of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with 1 to 5 fluorine atoms and/or 1 to 2 iodine atoms, a $C_3$-$C_{10}$ cycloalkyl radical optionally substituted with 1 to 5 fluorine atoms and/or 1 to 2 iodine atoms, a $C_2$-$C_{10}$ alkenyl radical optionally substituted with 1 to 5 fluorine atoms and/or 1 to 2 iodine atoms, a $C_3$-$C_{10}$ cycloalkenyl radical optionally substituted with 1 to 5 fluorine atoms and/or 1 to 2 iodine atoms, and a $C_6$-$C_{10}$ aryl radical optionally substituted with 1 to 5 fluorine atoms and/or 1 to 2 iodine atoms; on condition that at least one of the substituents $R^1$, $R^2$ or $R^3$ is F or is a radical as defined above comprising at least one fluorine atom; and on condition that said iodofluorocarbon compound A is not $CF_3I$.

More preferentially, said iodofluorocarbon compound A is of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with 1 to 5 fluorine atoms and/or 1 iodine atom, a $C_3$-$C_{10}$ cycloalkyl radical optionally substituted with 1 to 5 fluorine atoms and/or 1 iodine atom, a $C_2$-$C_{10}$ alkenyl radical optionally substituted with 1 to 5 fluorine atoms and/or 1 iodine atom, a $C_3$-$C_{10}$ cycloalkenyl radical optionally substituted with 1 to 5 fluorine atoms and/or 1 iodine atom, and a $C_6$-$C_{10}$ aryl radical optionally substituted with 1 to 5 fluorine atoms and/or 1 iodine atom; on condition that at least one of the substituents $R^1$, $R^2$ or $R^3$ is F or is a radical as defined above comprising at least one fluorine atom. Alternatively, said iodofluorocarbon compound A is of formula (I) $(R^1)(R^2)C(I)(R^3)$ or of formula (II) $(R^1)(R^2)C{=}C(I)(R^3)$; wherein wherein $R^1$, $R^2$ and $R^3$ are, independently of one another, selected from the group consisting of H, F, I, a $C_1$-$C_{10}$ alkyl radical optionally substituted with 1 to 5 fluorine atoms and/or 1 iodine atom, a $C_3$-$C_{10}$ cycloalkyl radical optionally substituted with 1 to 5 fluorine atoms and/or 1 iodine atom, a $C_2$-$C_{10}$ alkenyl radical optionally substituted with 1 to 5 fluorine atoms and/or 1 iodine atom, a $C_3$-$C_{10}$ cycloalkenyl radical optionally substituted with 1 to 5 fluorine atoms and/or 1 iodine atom, and a $C_6$-$C_{10}$ aryl radical optionally substituted with 1 to 5 fluorine atoms and/or 1 iodine atom; on condition that at least one of the substituents $R^1$, $R^2$ or $R^3$ is F or is a radical as defined above comprising at least one fluorine atom; and on condition that said iodofluorocarbon compound A is not $CF_3I$.

According to a preferred embodiment, said iodofluorocarbon compound A is of formula (I) or (II), wherein $R^1$, $R^2$ and $R^3$ are, independently of one another, selected from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; on condition that at least one of the substituents $R^1$, $R^2$ or $R^3$ is F or is a radical as defined here comprising at least one fluorine atom. In particular, said iodofluorocarbon compound A is of formula (I) or (II), wherein $R^1$, $R^2$ and $R^3$ are, independently of one another, selected from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; on condition that at least one of the substituents $R^1$, $R^2$ or $R^3$ is F or is a radical as defined here comprising at least one fluorine atom. According to a preferred embodiment, said iodofluorocarbon compound A is of formula (I) or (II), wherein $R^1$, $R^2$ and $R^3$ are, independently of one another, selected from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; on condition that at least one of the substituents $R^1$, $R^2$ or $R^3$ is F or is a radical as defined here comprising at least one fluorine atom; and on condition that said iodofluorocarbon compound A is not $CF_3I$. In particular, said iodofluorocarbon compound A is of formula (I) or (II), wherein $R^1$, $R^2$ and $R^3$ are, independently of one another, selected from the group consisting of H, F, I, a $C_1$-$C_5$ perfluoroalkyl radical, a $C_5$-$C_{10}$ perfluorocycloalkyl radical, a $C_2$-$C_5$perfluoroalkenyl radical, a $C_5$-$C_{10}$ perfluorocycloalkenyl radical, a $C_6$-$C_{10}$ perfluoroaryl radical; on condition that at least one of the substituents $R^1$, $R^2$ or $R^3$ is F or is a radical as defined here comprising at least one fluorine atom; and on condition that said iodofluorocarbon compound A is not $CF_3I$.

According to a preferred embodiment, said iodofluorocarbon compound A is of formula (I) or (II), wherein $R^1$, $R^2$ and $R^3$ are, independently of one another, selected from the group consisting of H, I, F or $Y^1$—[—$C(Y^2)(Y^3)$—]$_n$— wherein $Y^1$, $Y^2$, and $Y^3$ are, independently of one another and independently for each unit n, selected from the group consisting of H, I and F; and n is an integer from 1 to 10; on condition that at least one of the substituents $R^1$, $R^2$, $R^3$, $Y^1$, $Y^2$ or $Y^3$ is a fluorine atom. In particular, said iodofluorocarbon compound A is of formula (I) or (II), wherein $R^1$, $R^2$ and $R^3$ are, independently of one another, selected from the group consisting of H, I, F or $Y^1$—[—$C(Y^2)(Y^3)$—]$_n$— wherein $Y^1$, $Y^2$, and $Y^3$ are, independently of one another and independently for each unit n, selected from the group consisting of H, I and F; and n is an integer from 1 to 5; on condition that at least one of the substituents $R^1$, $R^2$, $R^3$, $Y^1$, $Y^2$ or $Y^3$ is a fluorine atom. According to a preferred embodiment, said iodofluorocarbon compound A is of formula (I) or (II), wherein $R^1$, $R^2$ and $R^3$ are, independently of one another, selected from the group consisting of H, I, F or $Y^1$—[—$C(Y^2)(Y^3)$—]$_n$— wherein $Y^1$, $Y^2$, and $Y^3$ are, independently of one another and independently for each unit n, selected from the group consisting of H, I and F; and n is an integer from 1 to 10; on condition that at least one of the substituents $R^1$, $R^2$, $R^3$, $Y^1$, $Y^2$ or $Y^3$ is a fluorine atom. In particular, said iodofluorocarbon compound A is of formula (I) or (II), wherein $R^1$, $R^2$ and $R^3$ are, independently of one another, selected from the group consisting of H, F or $Y^1$—[—$C(Y^2)(Y^3)$—]$_n$— wherein $Y^1$, $Y^2$, and $Y^3$ are, independently of one another and independently for each unit n, selected from the group consisting of H, I and F; and n is an integer from 1 to 5; on condition that at least one of the substituents $R^1$, $R^2$, $R^3$, $Y^1$, $Y^2$ or $Y^3$ is a fluorine atom; and on condition that said iodofluorocarbon compound A is not $CF_3I$.

According to another preferred embodiment, said iodofluorocarbon compound A is of formula (I) or (II), wherein $R^1$, $R^2$ and $R^3$ are, independently of one another, selected from the group consisting of H, F or $Y^1$—[—$C(Y^2)(Y^3)$—]$_n$— wherein $Y^1$, $Y^2$, and $Y^3$ are, independently of one another and independently for each unit n, selected from the group consisting of H, I and F; and n is an integer from 1 to 10; on condition that at least one of the substituents $R^1$, $R^2$, $R^3$, $Y^1$, $Y^2$ or $Y^3$ is a fluorine atom. In particular, said compound A is of formula (I) or (II), wherein $R^1$, $R^2$ and $R^3$ are, independently of one another, selected from the group consisting of H, F or $Y^1$—[—$C(Y^2)(Y^3)$—]$_n$— wherein $Y^1$, $Y^2$, and $Y^3$ are, independently of one another and independently for each unit n, selected from the group consisting of H, I and F; and n is an integer from 1 to 5; on condition that at least one of the substituents $R^1$, $R^2$, $R^3$, $Y^1$, $Y^2$ or $Y^3$ is a fluorine atom. According to another preferred embodiment, said iodofluorocarbon compound A is of formula (I) or (II), wherein $R^1$, $R^2$ and $R^3$ are, independently of one another, selected from the group consisting of H, F or $Y^1$—[—$C(Y^2)(Y^3)$—]$_n$— wherein $Y^1$, $Y^2$, and $Y^3$ are, independently of one another and independently for each unit n, selected from the group consisting of H, I and F; and n is an integer from 1 to 10; on condition that at least one of the substituents $R^1$, $R^2$, $R^3$, $Y^1$, $Y^2$ or $Y^3$ is a fluorine atom; and on condition that said iodofluorocarbon compound A is not $CF_3I$. In particular, said compound A is of formula (I) or (II), wherein $R^1$, $R^2$ and $R^3$ are, independently of one another, selected from the group consisting of H, F or $Y^1$—[—$C(Y^2)(Y^3)$—]$_n$— wherein $Y^1$, $Y^2$, and $Y^3$ are, independently of one another and independently for each unit n, selected from the group consisting of H, I and F; and n is an integer from 1 to 5; on condition that at least one of the substituents $R^1$, $R^2$, $R^3$, $Y^1$, $Y^2$ or $Y^3$ is a fluorine atom; and on condition that said iodofluorocarbon compound A is not $CF_3I$.

Preferably, said iodofluorocarbon compound A is selected from the group consisting of $CH_2FI$, $CHF_2I$, $CF_3I$, $CH_2F$—$CH_2I$, CHFI—$CH_3$, CFI=$CH_2$, cis-CHF=CHI, trans-CHF=CHI, $CHF_2$—$CH_2I$, $CF_2I$—$CH_3$, $CF_3$—$CH_2I$, $CF_2$=CHI, $CH_2F$—CHFI, cis-CFI=CHF, trans-CFI=CHF, $CHF_2$—CHFI, $CF_2I$—$CH_2F$, $CF_3$—CHFI, $CF_2$=CFI, $CHF_2$—$CF_2I$, $CF_2I$—$CF_3$, $CH_3$—CHF—$CH_2I$, $CH_3$—CFI—$CH_3$, $CH_3$—$CF_2$—$CH_2I$, $CH_2$=CF—$CH_2I$, cis-$CH_3$—CF=CHI, trans-$CH_3$—CF=CHI, $CH_3$—$CH_2$—CHFI, $CH_3$—CHI—$CH_2F$, $CH_2$=CH—CHFI, cis-$CH_3$—CI=CHF, trans-$CH_3$—CI=CHF, cis-$CH_3$—CH=CFI, trans-$CH_3$—CH=CFI, $CH_2F$—$CH_2$—$CH_2I$, cis-CHF=CH—$CH_2I$, trans-CHF=CH—$CH_2I$, $CH_2F$—CI=$CH_2$, cis-$CH_2F$—CH=CHI, trans-$CH_2F$—CH=CHI, $CH_3$—CHF—CHFI, $CH_3$—CFI—$CH_2F$, $CH_3$—$CF_2$—CHFI, $CH_2$=CF—CHFI, cis-$CH_3$—CF=CFI, trans-$CH_3$—CF=CFI, $CH_2F$—CHF—$CH_2I$, $CH_2F$—$CF_2$—$CH_2I$, cis-CHF=CF—$CH_2I$, trans-CHF=CF—$CH_2I$, cis-$CH_2F$—CF=CHI, trans-$CH_2F$—CF=CHI, $CH_3$—$CH_2$—$CF_2I$, $CH_3$—CHI—$CHF_2$, $CH_2$=CH—$CF_2I$, $CH_3$—CI=$CF_2$, $CH_2F$—$CH_2$—CHFI, $CH_2F$—CHI—$CH_2F$, cis-CHF=CH—CHFI, trans-CHF=CH—CHFI, cis-$CH_2F$—CI=CHF, trans-$CH_2F$—CI=CHF, cis-$CH_2F$—CH=CFI, trans-$CH_2F$—CH=CFI, $CHF_2$—$CH_2$—$CH_2I$, $CF_2$=CH—$CH_2I$, $CHF_2$—CI=$CH_2$, cis-$CHF_2$—CH=CHI, trans-$CHF_2$—CH=CHI, $CH_3$—CHF—$CF_2I$, $CH_3$—CFI—$CHF_2$, $CH_3$—$CF_2$—$CF_2I$, $CH_2$=CF—$CF_2I$, $CH_2F$—CHF—CHFI, $CH_2F$—CFI—$CH_2F$, $CH_2F$—$CF_2$—CHFI, cis-CHF=CF—CHFI, trans-CHF=CF—CHFI, cis-$CH_2F$—CF=CFI, trans-$CH_2F$—CF=CFI, $CHF_2$—CHF—$CH_2I$, $CHF_2$—$CF_2$—$CH_2I$, $CF_2$=CF—$CH_2I$, cis-$CHF_2$—CF=CHI, trans-$CHF_2$—CF=CHI, $CH_2F$—$CH_2$—$CF_2I$, $CH_2F$—CHI—$CHF_2$, cis-CHF=CH—$CF_2I$, trans-CHF=CH—$CF_2I$, $CH_2F$—CI=$CF_2$, $CHF_2$—$CH_2$—CHFI, $CF_2$=CH—CHFI, cis-$CHF_2$—CI=CHF, trans-$CHF_2$—CI=CHF, cis-$CHF_2$—CH=CFI, trans-$CHF_2$—CH=CFI, $CF_3$—$CH_2$—$CH_2I$, $CF_3$—CHI—$CH_3$, $CF_3$—CI=$CH_2$, cis-$CF_3$—CH=CHI, trans-$CF_3$—CH=CHI, $CH_2F$—CHF—$CF_2I$, $CH_2F$—CFI—$CHF_2$, $CH_2F$—$CF_2$—$CF_2I$, cis-CHF=CF—$CF_2I$, trans-CHF=CF—$CF_2I$, $CHF_2$—CHF—CHFI, $CHF_2$—$CF_2$—CHFI, $CF_2$=CF—CHFI, cis-$CHF_2$—CF=CFI, trans-$CHF_2$—CF=CFI, $CF_3$—CHF—$CH_2I$, $CF_3$—CFI—$CH_3$, $CF_3$—$CF_2$—$CH_2I$, cis-$CF_3$—CF=CHI, trans-$CF_3$—CF=CHI, $CHF_2$—$CH_2$—$CF_2I$, $CHF_2$—CHI—$CHF_2$, $CF_2$=CH—$CF_2I$, $CHF_2$—CI=$CF_2$, $CF_3$—$CH_2$—CHFI, $CF_3$—CHI—$CH_2F$, cis-$CF_3$—CI=CHF, trans-$CF_3$—CI=CHF, cis-$CF_3$—CH=CFI, trans-$CF_3$—CH=CFI, $CHF_2$—CHF—$CF_2I$, $CHF_2$—CFI—$CHF_2$, $CHF_2$—$CF_2$—$CF_2I$, $CF_2$=CF—$CF_2I$, $CF_3$—CHF—CHFI, $CF_3$—CFI—$CH_2F$, $CF_3$—$CF_2$—CHFI, cis-$CF_3$—CF=CFI, trans-$CF_3$—CF=CFI, $CF_3$—$CH_2$—$CF_2I$, $CF_3$—CHI—$CHF_2$, $CF_3$—CHI—$CF_3$, $CF_3$—CI=$CF_2$, $CF_3$—CHF—$CF_2I$, $CF_3$—CFI—$CHF_2$, $CF_3$—CFI—$CF_3$, $CF_3$—$CF_2$—$CF_2I$. More preferentially, said iodofluorocarbon compound A is selected from the group consisting of $CH_2FI$, $CHF_2I$, $CH_2F$—$CH_2I$, CHFI—$CH_3$, CFI=$CH_2$, cis-CHF=CHI, trans-CHF=CHI, $CHF_2$—$CH_2I$, $CF_2I$—$CH_3$, $CF_3$—$CH_2I$, $CF_2$=CHI, $CH_2F$—CHFI, cis-CFI=CHF, trans-CFI=CHF, $CHF_2$—CHFI, $CF_2I$—$CH_2F$, $CF_3$—CHFI, $CF_2$=CFI, $CHF_2$—$CF_2I$, $CF_2I$—$CF_3$, $CH_3$—CHF—$CH_2I$, $CH_3$—CFI—$CH_3$, $CH_3$—$CF_2$—$CH_2I$, $CH_2$=CF—$CH_2I$, cis-$CH_3$—CF=CHI, trans-$CH_3$—CF=CHI, $CH_3$—$CH_2$—CHFI, $CH_3$—CHI—$CH_2F$, $CH_2$=CH—CHFI, cis-$CH_3$—CI=CHF, trans-$CH_3$—CI=CHF, cis-$CH_3$—CH=CFI, trans-$CH_3$—CH=CFI, $CH_2F$—$CH_2$—$CH_2I$, cis-CHF=CH—$CH_2I$, trans-CHF=CH—$CH_2I$, $CH_2F$—CI=$CH_2$, cis-$CH_2F$—CH=CHI, trans-$CH_2F$—CH=CHI, $CH_3$—CHF—CHFI, $CH_3$—CFI—$CH_2F$, $CH_3$—$CF_2$—CHFI, $CH_2$=CF—CHFI, cis-$CH_3$—CF=CFI, trans-$CH_3$—CF=CFI, $CH_2F$—CHF—$CH_2I$, $CH_2F$—$CF_2$—$CH_2I$, cis-CHF=CF—$CH_2I$, trans-CHF=CF—$CH_2I$, cis-$CH_2F$—CF=CHI, trans-$CH_2F$—CF=CHI, $CH_3$—$CH_2$—$CF_2I$, $CH_3$—CHI—$CHF_2$, $CH_2$=CH—$CF_2I$, $CH_3$—CI=$CF_2$, $CH_2F$—$CH_2$—CHFI, $CH_2F$—CHI—$CH_2F$, cis-CHF=CH—CHFI, trans-CHF=CH—CHFI, cis-$CH_2F$—CI=CHF, trans-$CH_2F$—CI=CHF, cis-$CH_2F$—CH=CFI, trans-$CH_2F$—CH=CFI, $CHF_2$—$CH_2$—$CH_2I$, $CF_2$=CH—$CH_2I$, $CHF_2$—CI=$CH_2$, cis-$CHF_2$—CH=CHI, trans-$CHF_2$—CH=CHI, $CH_3$—CHF—$CF_2I$, $CH_3$—CFI—$CHF_2$, $CH_3$—$CF_2$—$CF_2I$, $CH_2$=CF—$CF_2I$, $CH_2F$—CHF—CHFI, $CH_2F$—CFI—$CH_2F$, $CH_2F$—$CF_2$—CHFI, cis-CHF=CF—CHFI, trans-CHF=CF—CHFI, cis-$CH_2F$—CF=CFI, trans-$CH_2F$—CF=CFI, $CHF_2$—CHF—$CH_2I$, $CHF_2$—$CF_2$—$CH_2I$, $CF_2$=CF—$CH_2I$, cis-$CHF_2$—CF=CHI, trans-$CHF_2$—CF=CHI, $CH_2F$—$CH_2$—$CF_2I$, $CH_2F$—CHI—$CHF_2$, cis-CHF=CH—$CF_2I$, trans-CHF=CH—$CF_2I$, $CH_2F$—CI=$CF_2$, $CHF_2$—$CH_2$—CHFI, $CF_2$=CH—CHFI, cis-$CHF_2$—CI=CHF, trans-$CHF_2$—CI=CHF, cis-$CHF_2$—CH=CFI, trans-$CHF_2$—CH=CFI, $CF_3$—$CH_2$—$CH_2I$, $CF_3$—CHI—$CH_3$, $CF_3$—CI=$CH_2$, cis-$CF_3$—CH=CHI, trans-$CF_3$—CH=CHI, $CH_2F$—CHF—$CF_2I$, $CH_2F$—CFI—$CHF_2$, $CH_2F$—$CF_2$—$CF_2I$, cis-CHF=CF—$CF_2I$, trans-CHF=CF—$CF_2I$, $CHF_2$—CHF—CHFI, $CHF_2$—$CF_2$—CHFI, $CF_2$=CF—CHFI, cis-$CHF_2$—CF=CFI, trans-$CHF_2$—CF=CFI, $CF_3$—CHF—$CH_2I$, $CF_3$—CFI—$CH_3$, $CF_3$—$CF_2$—$CH_2I$, cis-$CF_3$—CF=CHI, trans-$CF_3$—CF=CHI, $CHF_2$—$CH_2$—$CF_2I$, $CHF_2$—CHI—$CHF_2$, $CF_2$=CH—$CF_2I$, $CHF_2$—CI=$CF_2$, $CF_3$—$CH_2$—CHFI, $CF_3$—CHI—$CH_2F$, cis-$CF_3$—CI=CHF, trans-$CF_3$—CI=CHF, cis-$CF_3$—CH=CFI, trans-$CF_3$—CH=CFI, $CHF_2$—CHF—$CF_2I$, $CHF_2$—CFI—$CHF_2$, $CHF_2$—$CF_2$—$CF_2I$, $CF_2$=CF—$CF_2I$, $CF_3$—CHF—CHFI, $CF_3$—CFI—$CH_2F$, $CF_3$—$CF_2$—CHFI, cis-$CF_3$—CF=CFI, trans-$CF_3$—CF=CFI, $CF_3$—$CH_2$—$CF_2I$, $CF_3$—CHI—$CHF_2$, $CF_3$—CHI—$CF_3$, $CF_3$—CI=$CF_2$, $CF_3$—CHF—$CF_2I$, $CF_3$—CFI—$CHF_2$, $CF_3$—CFI—$CF_3$, $CF_3$—$CF_2$—$CF_2I$.

In particular, said iodofluorocarbon compound A is selected from the group consisting of $CHF_2I$, $CF_3I$, $CHF_2$—$CH_2I$, $CF_2I$—$CH_3$, $CF_3$—$CH_2I$, $CF_2$=CHI, $CHF_2$—CHFI, $CF_2I$—$CH_2F$, $CF_3$—CHFI, $CF_2$=CFI, $CHF_2$—$CF_2I$, $CF_2I$—$CF_3$, $CF_3$—$CH_2$—$CH_2I$, $CF_3$—CHI—$CH_3$, $CF_3$—CI=$CH_2$, cis-$CF_3$—CH=CHI, trans-$CF_3$—CH=CHI, $CF_3$—CHF—$CH_2I$, $CF_3$—CFI—$CH_3$, $CF_3$—$CF_2$—$CH_2I$, cis-$CF_3$—CF=CHI, trans-$CF_3$—CF=CHI, $CF_3$—$CH_2$—CHFI, $CF_3$—CHI—$CH_2F$, cis-$CF_3$—CI=CHF, trans-$CF_3$—CI=CHF, cis-$CF_3$—CH=CFI, trans-$CF_3$—CH=CFI, $CF_3$—CHF—CHFI, $CF_3$—CFI—$CH_2F$, $CF_3$—$CF_2$—CHFI, cis-$CF_3$—CF=CFI, trans-$CF_3$—CF=CFI, $CF_3$—CHF—$CF_2I$, $CF_3$—CFI—$CHF_2$, $CF_3$—CFI—$CF_3$, $CF_3$—$CF_2$—$CF_2I$. More particularly, said iodofluorocarbon compound A is selected from the group consisting of $CHF_2I$, $CHF_2$—$CH_2I$, $CF_2I$—$CH_3$, $CF_3$—$CH_2I$, $CF_2$=CHI, $CHF_2$—CHFI, $CF_2I$—$CH_2F$, $CF_3$—CHFI, $CF_2$=CFI, $CHF_2$—$CF_2I$, $CF_2I$—$CF_3$, $CF_3$—$CH_2$—$CH_2I$, $CF_3$—CHI—$CH_3$, $CF_3$—CI=$CH_2$, cis-$CF_3$—CH=CHI, trans-$CF_3$—CH=CHI, $CF_3$—CHF—$CH_2I$, $CF_3$—CFI—$CH_3$, $CF_3$—$CF_2$—$CH_2I$, cis-$CF_3$—CF=CHI, trans-$CF_3$—CF=CHI, $CF_3$—$CH_2$—CHFI, $CF_3$—CHI—$CH_2F$, cis-$CF_3$—CI=CHF, trans-$CF_3$—CI=CHF, cis-$CF_3$—CH=CFI, trans-$CF_3$—CH=CFI, $CF_3$—CHF—CHFI, $CF_3$—CFI—$CH_2F$, $CF_3$—$CF_2$—CHFI, cis-$CF_3$—CF=CFI, trans-$CF_3$—CF=CFI, $CF_3$—CHF—$CF_2I$, $CF_3$—CFI—$CHF_2$, $CF_3$—CFI—$CF_3$, $CF_3$—$CF_2$—$CF_2I$.

Alternatively, said iodofluorocarbon compound A is selected from the group consisting of $CHFI_2$, $CF_2I_2$, $CFI_2$—$CH_3$, $CH_2F$—$CHI_2$, CHFI—$CH_2I$, $CHF_2$—$CHI_2$, $CF_2I$—$CH_2I$, $CFI_2$—$CH_2F$, CHFI—CHFI, $CF_3$—$CHI_2$, $CHF_2$—$CFI_2$, $CF_2I$—CHFI, $CF_3$—$CFI_2$, $CF_2I$—$CF_2I$, $CFI_2$—$CH_2$—$CH_3$, $CH_2F$—$CI_2$—$CH_3$, $CH_2F$—$CH_2$—$CHI_2$, $CHFI—CHI—CH_3$,$CHFI—CH_2—CH_2I$, $CH_2F—CHI—CH_2I$, $CHI_2—CHF—CH_3$, $CH_2I—CFI—CH_3$, $CH_2I—CHF—CH_2I$, $CFI_2—CH_2—CH_2F$, $CH_2F—CI_2—CH_2F$, $CHFI—CHI—CH_2F$, $CHFI—CH_2—CHFI$, $CHF_2—CI_2—CH_3$, $CHF_2—CH_2—CHI_2$, $CF_2I—CHI—CH_3$, $CF_2I—CH_2—CH_2I$, $CHF_2—CHI—CH_2I$, $CFI_2—CHF—CH_3$, $CH_2F—CHF—CHI_2$, $CHFI—CFI—CH_3$, $CHFI—CHF—CH_2I$, $CH_2F—CFI—CH_2I$, $CHI_2—CF_2—CH_3$, $CH_2I—CF_2—CH_2I$, $CHF_2—CI_2—CH_2F$, $CHF_2—CH_2—CFI_2$, $CF_2I—CHI—CH_2F$, $CF_2I—CH_2—CHFI$, $CHF_2—CHI—CHFI$, $CF_3—CI_2—CH_3$, $CF_3—CH_2—CHI_2$, $CF_3—CHI—CH_2I$, $CFI_2—CHF—CH_2F$, $CHFI—CFI—CH_2F$, $CHFI—CHF—CHFI$, $CHF_2—CHF—CHI_2$, $CF_2I—CFI—CH_3$, $CF_2I—CHF—CH_2I$, $CHF_2—CFI—CH_2I$, $CFI_2—CF_2—CH_3$, $CH_2F—CF_2—CHI_2$, $CHFI—CF_2—CH_2I$, $CHF_2—CI_2—CHF_2$, $CF_2I—CHI—CHF_2$, $CF_2I—CH_2—CF_2I$, $CF_3—CI_2—CH_2F$, $CF_3—CH_2—CFI_2$, $CF_3—CHI—CHFI$, $CHF_2—CHF—CFI_2$, $CF_2I—CFI—CH_2F$, $CF_2I—CHF—CHFI$, $CHF_2—CFI—CHFI$, $CF_3—CHF—CHI_2$, $CF_3—CFI—CH_2I$, $CFI_2—CF_2—CH_2F$, $CHFI—CF_2—CHFI$, $CHF_2—CF_2—CHI_2$, $CF_2I—CF_2—CH_2I$, $CF_3—CI_2—CHF_2$, $CF_3—CHI—CF_2I$, $CF_2I—CFI—CHF_2$, $CF_2I—CHF—CF_2I$, $CF_3—CHF—CFI_2$, $CF_3—CFI—CHFI$, $CHF_2—CF_2—CFI_2$, $CF_2I—CF_2—CHFI$, $CF_3—CF_2—CHI_2$, $CF_3—CI_2—CF_3$, $CF_3—CFI—CF_2I$, $CF_2I—CF_2—CF_2I$, $CF_3—CF_2—CFI_2$.

In particular, said iodofluorocarbon compound A is selected from the group consisting of $CF_2I_2$, $CHF_2—CHI_2$, $CF_2I—CH_2I$, $CF_3—CHI_2$, $CF_3—CFI_2$, $CFI_2—CHF—CH_3$, $CH_2F—CHF—CHI_2$, $CHFI—CFI—CH_3$, $CHFI—CHF—CH_2I$, $CH_2F—CFI—CH_2I$, $CF_3—CI_2—CH_3$, $CF_3—CH_2—CHI_2$, $CF_3—CHI—CH_2I$, $CF_3—CI_2—CH_2F$, $CF_3—CH_2—CFI_2$, $CF_3—CHI—CHFI$, $CF_3—CHF—CHI_2$, $CF_3—CFI—CH_2I$, $CF_3—CI_2—CHF_2$, $CF_3—CHI—CF_2I$, $CF_3—CHF—CFI_2$, $CF_3—CFI—CHFI$, $CF_3—CI_2—CF_3$, $CF_3—CFI—CF_2I$, $CF_2I—CHFI$.

Said composition also comprises at least one compound B. Said at least one compound B is selected from the group consisting of water, HF, HI, $IF_5$, $I_2$, $O_2$, $CO_2$, CO and nitrogen or a mixture thereof. In said composition, said at least one compound B represents at most 0.5% by weight on the basis of the total weight of the composition, advantageously at most 0.4% by weight, preferably at most 0.3% by weight, more preferentially at most 0.2% by weight, in particular at most 0.1% by weight, more particularly at most 0.05% by weight on the basis of the total weight of the composition. When said composition comprises two or more compounds B, as defined above, the weight content expressed above applies for all of the compounds B present. Thus, the sum of the weight contents of each of the compounds B present in the composition is at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm on the basis of the total weight of the composition. Compositions comprising at most 1000 ppm of compounds B as defined above are favored for the intended applications. Specifically, compositions according to the present invention comprising at most 1000 ppm of water or at most 1000 ppm of $O_2$ limit or prevent the degradation or the polymerization of the compound A.

Thus, in addition to compound A, said composition may comprise two compounds B as defined above or three compounds B as defined above or four compounds B as defined above or five compounds B as defined above or six compounds B as defined above or seven compounds B as defined above or eight compounds B as defined above or nine compounds B as defined above. Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of water on the basis of the total weight of the composition.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of HI on the basis of the total weight of the composition.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of HF on the basis of the total weight of the composition.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of $IF_5$ on the basis of the total weight of the composition.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of $1_2$ on the basis of the total weight of the composition.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of $O_2$ on the basis of the total weight of the composition.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of $CO_2$ on the basis of the total weight of the composition.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of CO on the basis of the total weight of the composition.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of nitrogen on the basis of the total weight of the composition.

Favorably, compound B is selected from the group consisting of water, $O_2$, $CO_2$, CO and nitrogen or a mixture thereof. Preferably, said composition is free of HF, HI, $IF_5$ and $I_2$. The term "free of" refers to a weight content in the designated compound of less than 1 ppm on the basis of the total weight of the composition. Specifically, the absence of acidity in the composition is favored for the intended applications.

Said composition according to the present invention may therefore comprise at least 99.5% by weight of an iodofluorocarbon compound A and at most 0.5% by weight of at least one compound B chosen from water, $O_2$, $CO_2$, CO and nitrogen or a mixture thereof. Thus, in addition to compound A, said composition may comprise two compounds B chosen from water, $O_2$, $CO_2$, CO and nitrogen; or three compounds B chosen from water, $O_2$, $CO_2$, CO and nitrogen; or four compounds B chosen from water, $O_2$, $CO_2$, CO and nitrogen; or five compounds B chosen from water, $O_2$, $CO_2$, CO and nitrogen; in any one of the contents mentioned above for compound B. For example, in addition to compound A, said composition may comprise water and $O_2$ or water and nitrogen, or water and $CO_2$ or water and CO or water, $O_2$ and nitrogen or water, $O_2$ and $CO_2$; in any one of the contents mentioned above for compound B.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of water and $O_2$ on the basis of the total weight of the composition. The weight content mentioned is based on the sum of the individual contents of water and $O_2$. Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of water and nitrogen on the basis of the total weight of the composition. The weight content mentioned is based on the sum of the individual contents of water and nitrogen.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of water and $CO_2$ on the basis of the total weight of the composition. The weight content mentioned is based on the sum of the individual contents of water and $CO_2$. Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of water and CO on the basis of the total weight of the composition. The weight content mentioned is based on the sum of the individual contents of water and CO. Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of water, nitrogen and $O_2$ on the basis of the total weight of the composition. The weight content mentioned is based on the sum of the individual contents of water, nitrogen and $O_2$.

Said composition may comprise at least 99.5% by weight, advantageously at least 99.6% by weight, preferably at least 99.7% by weight, more preferentially at least 99.8% by weight, in particular at least 99.9% by weight, more particularly at least 99.95% by weight of an iodofluorocarbon compound A as defined above and at most 0.5% by weight, advantageously at most 0.4% by weight, preferably at most 0.3% by weight, more preferentially at most 0.2% by weight, in particular at most 0.1% by weight, more particularly at most 0.05% by weight, favorably at most 1000 ppm, advantageously favorably at most 100 ppm, preferentially favorably at most 10 ppm of water, $CO_2$ and $O_2$ on the basis of the total weight of the composition. The weight content mentioned is based on the sum of the individual contents of water, $CO_2$ and $O_2$.

Tables 1a to 37a below describe particular compositions in which said composition comprises the iodofluorocarbon compound A mentioned and the compound(s) B indicated, in the contents indicated. Each row of the table represents a particular composition comprising the compound A specified and one or more compounds B specified, in the content indicated. A blank cell indicates that the composition is free of the compound B specified, i.e. a content of less than 1 ppm of the compound B considered. Each composition described in a table, the weight content of compound A is at least 99.5% by weight, advantageously at least 99.6% by weight, preferably at least 99.7% by weight, more preferentially at least 99.8% by weight, in particular at least 99.9% by weight, more particularly at least 99.95% by weight on the basis of the total weight of the composition. The expression "1 ppm –100 ppm" signifies that the compound B indicated is present in the composition in a content of from 1 ppm to 100 ppm.

For example, in table 1 below, the sixth row describes a composition comprising at least 99.5% by weight, advantageously at least 99.6% by weight, preferably at least 99.7% by weight, more preferentially at least 99.8% by weight, in particular at least 99.9% by weight, more particularly at least 99.95% by weight of $CHF_2I$, from 1 ppm to 100 ppm of $H_2O$ and from 1 ppm to 100 ppm of $O_2$ on the basis of the total weight of the composition.

TABLE 1a

| Compound | Compound B | | | | |
|---|---|---|---|---|---|
| A | $H_2O$ | $O_2$ | $CO_2$ | CO | Nitrogen |
| $CHF_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 2a

| Compound | Compound B | | | | |
|---|---|---|---|---|---|
| A | $H_2O$ | $O_2$ | $CO_2$ | CO | Nitrogen |
| $CF_3I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 3a

| Compound | Compound B | | | | |
|---|---|---|---|---|---|
| A | $H_2O$ | $O_2$ | $CO_2$ | CO | Nitrogen |
| $CHF_2—CH_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 4a

| Compound | Compound B | | | | |
|---|---|---|---|---|---|
| A | $H_2O$ | $O_2$ | $CO_2$ | CO | Nitrogen |
| $CF_2I—CH_3I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 5a

| Compound | Compound B | | | | |
|---|---|---|---|---|---|
| A | $H_2O$ | $O_2$ | $CO_2$ | CO | Nitrogen |
| $CF_3—CH_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 6a

| Compound | Compound B | | | | |
|---|---|---|---|---|---|
| A | $H_2O$ | $O_2$ | $CO_2$ | CO | Nitrogen |
| $CF_2$=CHI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 7a

| Compound | Compound B | | | | |
|---|---|---|---|---|---|
| A | $H_2O$ | $O_2$ | $CO_2$ | CO | Nitrogen |
| $CHF_2$—CHFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 8a

| Compound | Compound B | | | | |
|---|---|---|---|---|---|
| A | $H_2O$ | $O_2$ | $CO_2$ | CO | Nitrogen |
| $CF_2I$—$CH_2F$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 9a

| Compound | Compound B | | | | |
|---|---|---|---|---|---|
| A | $H_2O$ | $O_2$ | $CO_2$ | CO | Nitrogen |
| $CF_3$—CHFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 10a

| Compound | Compound B | | | | |
|---|---|---|---|---|---|
| A | $H_2O$ | $O_2$ | $CO_2$ | CO | Nitrogen |
| $CF_2$═CFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 11a

| Compound | Compound B | | | | |
|---|---|---|---|---|---|
| A | $H_2O$ | $O_2$ | $CO_2$ | CO | Nitrogen |
| $CHF_2$—$CF_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 12a

| Compound | Compound B | | | | |
|---|---|---|---|---|---|
| A | $H_2O$ | $O_2$ | $CO_2$ | CO | Nitrogen |
| $CF_2I—CF_3$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 13a

| Compound | Compound B | | | | |
|---|---|---|---|---|---|
| A | $H_2O$ | $O_2$ | $CO_2$ | CO | Nitrogen |
| $CF_3—CH_2—CH_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 14a

| Compound | Compound B | | | | |
|---|---|---|---|---|---|
| A | $H_2O$ | $O_2$ | $CO_2$ | CO | Nitrogen |
| $CF_3$—CHI—$CH_3$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 15a

| Compound | Compound B | | | | |
|---|---|---|---|---|---|
| A | $H_2O$ | $O_2$ | $CO_2$ | CO | Nitrogen |
| $CF_3$—CI═$CH_2$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 16a

| Compound A | Compound B $H_2O$ | $O_2$ | $CO_2$ | CO | Nitrogen |
|---|---|---|---|---|---|
| cis—$CF_3$—CH═CHI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 17a

| Compound A | Compound B $H_2O$ | $O_2$ | $CO_2$ | CO | Nitrogen |
|---|---|---|---|---|---|
| trans-$CF_3$—CH═CHI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 18a

| Compound | Compound B | | | | |
|---|---|---|---|---|---|
| A | $H_2O$ | $O_2$ | $CO_2$ | CO | Nitrogen |
| $CF_3$—CHF—$CH_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 19a

| Compound | Compound B | | | | |
|---|---|---|---|---|---|
| A | $H_2O$ | $O_2$ | $CO_2$ | CO | Nitrogen |
| $CF_3$—CFI—$CH_3$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 20a

| Compound A | Compound B | | | | |
|---|---|---|---|---|---|
| | $H_2O$ | $O_2$ | $CO_2$ | CO | Nitrogen |
| $CF_3$—$CF_2$—$CH_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 21a

| Compound A | Compound B | | | | |
|---|---|---|---|---|---|
| | $H_2O$ | $O_2$ | $CO_2$ | CO | Nitrogen |
| cis—$CF_3$—CF═CHI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 22a

| Compound | Compound B | | | | |
|---|---|---|---|---|---|
| A | $H_2O$ | $O_2$ | $CO_2$ | CO | Nitrogen |
| trans-$CF_3$—CF═CHI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 23a

| Compound | Compound B | | | | |
|---|---|---|---|---|---|
| A | $H_2O$ | $O_2$ | $CO_2$ | CO | Nitrogen |
| $CF_3$—$CH_2$—CHFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 24a

| Compound | Compound B | | | | |
|---|---|---|---|---|---|
| A | $H_2O$ | $O_2$ | $CO_2$ | CO | Nitrogen |
| $CF_3$—CHI—$CH_2F$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 25a

| Compound | Compound B | | | | |
|---|---|---|---|---|---|
| A | $H_2O$ | $O_2$ | $CO_2$ | CO | Nitrogen |
| cis-$CF_3$—CI═CHF | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 26a

| Compound | Compound B | | | | |
|---|---|---|---|---|---|
| A | $H_2O$ | $O_2$ | $CO_2$ | CO | Nitrogen |
| trans-$CF_3$—Cl═CHF | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 27a

| Compound | Compound B | | | | |
|---|---|---|---|---|---|
| A | $H_2O$ | $O_2$ | $CO_2$ | CO | Nitrogen |
| cis-$CF_3$—CH═CFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 28a

| Compound | Compound B | | | | |
|---|---|---|---|---|---|
| A | $H_2O$ | $O_2$ | $CO_2$ | CO | Nitrogen |
| trans-$CF_3$—CH═CFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 29a

| Compound | Compound B | | | | |
|---|---|---|---|---|---|
| A | $H_2O$ | $O_2$ | $CO_2$ | CO | Nitrogen |
| $CF_3$—CHF—CHFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 30a

| Compound A | Compound B $H_2O$ | $O_2$ | $CO_2$ | CO | Nitrogen |
|---|---|---|---|---|---|
| $CF_3$—CFI—$CH_2F$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 31a

| Compound A | Compound B $H_2O$ | $O_2$ | $CO_2$ | CO | Nitrogen |
|---|---|---|---|---|---|
| $CF_3$—$CF_2$—CHFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 32a

| | Compound B | | | | |
|---|---|---|---|---|---|
| Compound A | $H_2O$ | $O_2$ | $CO_2$ | CO | Nitrogen |
| cis—$CF_3$—CF═CFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 33a

| | Compound B | | | | |
|---|---|---|---|---|---|
| Compound A | $H_2O$ | $O_2$ | $CO_2$ | CO | Nitrogen |
| trans-$CF_3$—CF═CFI | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 34a

| | Compound B | | | | |
|---|---|---|---|---|---|
| Compound A | $H_2O$ | $O_2$ | $CO_2$ | CO | Nitrogen |
| $CF_3$—CHF—$CF_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 35a

| | Compound B | | | | |
|---|---|---|---|---|---|
| Compound A | $H_2O$ | $O_2$ | $CO_2$ | CO | Nitrogen |
| $CF_3$—CFI—$CHF_2$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 36a

| | Compound B | | | | |
|---|---|---|---|---|---|
| Compound A | $H_2O$ | $O_2$ | $CO_2$ | CO | Nitrogen |
| $CF_3$—CFI—$CF_3$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

TABLE 37a

| | Compound B | | | | |
|---|---|---|---|---|---|
| Compound A | $H_2O$ | $O_2$ | $CO_2$ | CO | Nitrogen |
| $CF_3$—$CF_2$—$CF_2I$ | 1 ppm-100 ppm | | | | |
| | | 1 ppm-100 ppm | | | |
| | | | 1 ppm-100 ppm | | |
| | | | | 1 ppm-100 ppm | |
| | | | | | 1 ppm-100 ppm |
| | 1 ppm-100 ppm | 1 ppm-100 ppm | | | |
| | 1 ppm-100 ppm | | 1 ppm-100 ppm | | |
| | 1 ppm-100 ppm | | | 1 ppm-100 ppm | |
| | 1 ppm-100 ppm | | | | 1 ppm-100 ppm |
| | 1 ppm-100 ppm | 1 ppm-100 ppm | 1 ppm-100 ppm | | |
| | 1 ppm-100 ppm | 1 ppm-100 ppm | | 1 ppm-100 ppm | |
| | 1 ppm-100 ppm | 1 ppm-100 ppm | | | 1 ppm-100 ppm |
| | 1 ppm-100 ppm | | 1 ppm-100 ppm | 1 ppm-100 ppm | |
| | 1 ppm-100 ppm | | 1 ppm-100 ppm | | 1 ppm-100 ppm |
| | 1 ppm-100 ppm | | | 1 ppm-100 ppm | 1 ppm-100 ppm |
| | 1 ppm-100 ppm | 1 ppm-100 ppm | 1 ppm-100 ppm | 1 ppm-100 ppm | |
| | 1 ppm-100 ppm | 1 ppm-100 ppm | 1 ppm-100 ppm | | 1 ppm-100 ppm |
| | 1 ppm-100 ppm | | 1 ppm-100 ppm | 1 ppm-100 ppm | 1 ppm-100 ppm |
| | 1 ppm-100 ppm | 1 ppm-100 ppm | 1 ppm-100 ppm | 1 ppm-100 ppm | 1 ppm-100 ppm |
| | | 1 ppm-100 ppm | 1 ppm-100 ppm | | |
| | | 1 ppm-100 ppm | | 1 ppm-100 ppm | |
| | | 1 ppm-100 ppm | | | 1 ppm-100 ppm |
| | | 1 ppm-100 ppm | 1 ppm-100 ppm | 1 ppm-100 ppm | |
| | | 1 ppm-100 ppm | 1 ppm-100 ppm | | 1 ppm-100 ppm |
| | | 1 ppm-100 ppm | | 1 ppm-100 ppm | 1 ppm-100 ppm |
| | | 1 ppm-100 ppm | 1 ppm-100 ppm | 1 ppm-100 ppm | 1 ppm-100 ppm |
| | | | 1 ppm-100 ppm | 1 ppm-100 ppm | |
| | | | 1 ppm-100 ppm | | 1 ppm-100 ppm |
| | | | 1 ppm-100 ppm | 1 ppm-100 ppm | 1 ppm-100 ppm |
| | | | | 1 ppm-100 ppm | 1 ppm-100 ppm |

The compositions indicated in tables 1a to 37a are particularly appropriate for use as refrigerant, solvent, foam blowing agent, aerosol propellant, fire extinguisher, desiccant, in order to eliminate the water adsorbed on the surface of solid parts, and degreasing and cleaning agent for various surfaces, in particular as precision cleaning agent.

Regardless of the embodiment, the composition according to the invention may also comprise at most 6000 ppm, preferably at most 3000 ppm and in particular at most 1000 ppm of total organic impurities.

If necessary, the composition according to the invention can be purified to remove or reduce the content in at least one compound B or in another organic impurity. The purification can be carried out by:

- distillation: azeotropic distillation, extractive distillation or distillation under pressure;
- adsorption on solid: adsorption on molecular sieves (from 3A to 5A), zeolites, alumina, activated alumina or activated carbon;
- membrane separation;
- washing with water, sodium hydroxide and/or potassium hydroxide;
- chemical treatment, oxidation, chlorination, photochlorination.

Thus, compositions comprising said compound A and from 1 ppm to 10 ppm of at least one compound B can be obtained. Tables lb to 37b give details of the various compositions, according to the present invention, favorably obtained. The compositions indicated in tables 1b to 37b are particularly appropriate for use as refrigerant, solvent, foam blowing agent, aerosol propellant, fire extinguisher, desiccant, in order to eliminate the water adsorbed on the surface of solid parts, and degreasing and cleaning agent for various surfaces, in particular as precision cleaning agent.

TABLE 1b

| | Compound B | | | | |
|---|---|---|---|---|---|
| Compound A | $H_2O$ | $O_2$ | $CO_2$ | CO | Nitrogen |
| $CHF_2I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 2b

| | Compound B | | | | |
|---|---|---|---|---|---|
| Compound A | $H_2O$ | $O_2$ | $CO_2$ | CO | Nitrogen |
| $CF_3I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |

TABLE 2b-continued

| | Compound B | | | | |
|---|---|---|---|---|---|
| Compound A | $H_2O$ | $O_2$ | $CO_2$ | CO | Nitrogen |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 3b

| | Compound B | | | | |
|---|---|---|---|---|---|
| Compound A | $H_2O$ | $O_2$ | $CO_2$ | CO | Nitrogen |
| $CHF_2$—$CH_2I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 4b

| | Compound B | | | | |
|---|---|---|---|---|---|
| Compound A | $H_2O$ | $O_2$ | $CO_2$ | CO | Nitrogen |
| $CF_2I$—$CH_3I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |

TABLE 4b-continued

| | Compound B | | | | |
|---|---|---|---|---|---|
| Compound A | $H_2O$ | $O_2$ | $CO_2$ | CO | Nitrogen |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 5b

| | Compound B | | | | |
|---|---|---|---|---|---|
| Compound A | $H_2O$ | $O_2$ | $CO_2$ | CO | Nitrogen |
| $CF_3$—$CH_2I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 6b

| | Compound B | | | | |
|---|---|---|---|---|---|
| Compound A | $H_2O$ | $O_2$ | $CO_2$ | CO | Nitrogen |
| $CF_2$=CHI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 7b

| | Compound B | | | | |
|---|---|---|---|---|---|
| Compound A | $H_2O$ | $O_2$ | $CO_2$ | CO | Nitrogen |
| $CHF_2$—CHFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 8b

| Compound | Compound B | | | | |
|---|---|---|---|---|---|
| A | $H_2O$ | $O_2$ | $CO_2$ | CO | Nitrogen |
| $CF_2I$—$CH_2F$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 9b

| Compound | Compound B | | | | |
|---|---|---|---|---|---|
| A | $H_2O$ | $O_2$ | $CO_2$ | CO | Nitrogen |
| $CF_3$—CHFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 10b

| Compound | Compound B | | | | |
|---|---|---|---|---|---|
| A | $H_2O$ | $O_2$ | $CO_2$ | CO | Nitrogen |
| $CF_2$═CFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 11b

| Compound | Compound B | | | | |
|---|---|---|---|---|---|
| A | $H_2O$ | $O_2$ | $CO_2$ | CO | Nitrogen |
| $CHF_2$—$CF_2I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 12b

| Compound | Compound B | | | | |
|---|---|---|---|---|---|
| A | $H_2O$ | $O_2$ | $CO_2$ | CO | Nitrogen |
| $CF_2I—CF_3$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 13b

| Compound | Compound B | | | | |
|---|---|---|---|---|---|
| A | $H_2O$ | $O_2$ | $CO_2$ | CO | Nitrogen |
| $CF_3—CH_2—CH_2I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 14b

| Compound | Compound B | | | | |
|---|---|---|---|---|---|
| A | $H_2O$ | $O_2$ | $CO_2$ | CO | Nitrogen |
| $CF_3$—CHI $CH_3$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 15b

| Compound | Compound B | | | | |
|---|---|---|---|---|---|
| A | $H_2O$ | $O_2$ | $CO_2$ | CO | Nitrogen |
| $CF_3$—CI=$CH_2$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 16b

| Compound | Compound B | | | | |
|---|---|---|---|---|---|
| A | $H_2O$ | $O_2$ | $CO_2$ | CO | Nitrogen |
| cis-$CF_3$—CH═CHI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 17b

| Compound | Compound B | | | | |
|---|---|---|---|---|---|
| A | $H_2O$ | $O_2$ | $CO_2$ | CO | Nitrogen |
| trans-$CF_3$—CH═CHI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 18b

| Compound | Compound B | | | | |
|---|---|---|---|---|---|
| A | $H_2O$ | $O_2$ | $CO_2$ | CO | Nitrogen |
| $CF_3$—CHF—$CH_2I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 19b

| Compound | Compound B | | | | |
|---|---|---|---|---|---|
| A | $H_2O$ | $O_2$ | $CO_2$ | CO | Nitrogen |
| $CF_3$—CFI—$CH_3$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 20b

| Compound | Compound B | | | | |
|---|---|---|---|---|---|
| A | $H_2O$ | $O_2$ | $CO_2$ | CO | Nitrogen |
| $CF_3$—$CF_2$—$CH_2I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 21b

| Compound | Compound B | | | | |
|---|---|---|---|---|---|
| A | $H_2O$ | $O_2$ | $CO_2$ | CO | Nitrogen |
| cis-$CF_3$—CF═CHI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 22b

| Compound A | Compound B: $H_2O$ | $O_2$ | $CO_2$ | CO | Nitrogen |
|---|---|---|---|---|---|
| trans-$CF_3$—CF═CHI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 23b

| Compound A | Compound B: $H_2O$ | $O_2$ | $CO_2$ | CO | Nitrogen |
|---|---|---|---|---|---|
| $CF_3$—$CH_2$—CHFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 24b

| Compound | Compound B | | | | |
|---|---|---|---|---|---|
| A | $H_2O$ | $O_2$ | $CO_2$ | CO | Nitrogen |
| $CF_3$—CHI—$CH_2F$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 25b

| Compound | Compound B | | | | |
|---|---|---|---|---|---|
| A | $H_2O$ | $O_2$ | $CO_2$ | CO | Nitrogen |
| cis—$CF_3$—CI═CHF | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 26b

| Compound | Compound B | | | | |
|---|---|---|---|---|---|
| A | $H_2O$ | $O_2$ | $CO_2$ | CO | Nitrogen |
| trans—$CF_3$—Cl═CHF | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 27b

| Compound | Compound B | | | | |
|---|---|---|---|---|---|
| A | $H_2O$ | $O_2$ | $CO_2$ | CO | Nitrogen |
| cis—$CF_3$—CH═CFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 28b

| Compound | Compound B | | | | |
|---|---|---|---|---|---|
| A | $H_2O$ | $O_2$ | $CO_2$ | CO | Nitrogen |
| trans—$CF_3$—CH═CFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 29b

| Compound | Compound B | | | | |
|---|---|---|---|---|---|
| A | $H_2O$ | $O_2$ | $CO_2$ | CO | Nitrogen |
| $CF_3$—CHF—CHFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 30b

| Compound A | Compound B | | | | |
|---|---|---|---|---|---|
| | $H_2O$ | $O_2$ | $CO_2$ | CO | Nitrogen |
| $CF_3$—CFI—$CH_2F$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 31b

| Compound A | Compound B | | | | |
|---|---|---|---|---|---|
| | $H_2O$ | $O_2$ | $CO_2$ | CO | Nitrogen |
| $CF_3$—CF2—CHFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 32b

| Compound | Compound B | | | | |
|---|---|---|---|---|---|
| A | $H_2O$ | $O_2$ | $CO_2$ | CO | Nitrogen |
| cis—$CF_3$—CF═CFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 33b

| Compound | Compound B | | | | |
|---|---|---|---|---|---|
| A | $H_2O$ | $O_2$ | $CO_2$ | CO | Nitrogen |
| trans—$CF_3$—CF═CFI | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 34b

| Compound A | Compound B: $H_2O$ | $O_2$ | $CO_2$ | CO | Nitrogen |
|---|---|---|---|---|---|
| $CF_3$—CHF— | 1 ppm-10 ppm | | | | |
| $CF_2I$ | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 35b

| Compound A | Compound B: $H_2O$ | $O_2$ | $CO_2$ | CO | Nitrogen |
|---|---|---|---|---|---|
| $CF_3$—CFI— | 1 ppm-10 ppm | | | | |
| $CHF_2$ | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 36b

| Compound | Compound B | | | | |
|---|---|---|---|---|---|
| A | $H_2O$ | $O_2$ | $CO_2$ | CO | Nitrogen |
| $CF_3$—CFI—$CF_3$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

TABLE 37b

| Compound | Compound B | | | | |
|---|---|---|---|---|---|
| A | $H_2O$ | $O_2$ | $CO_2$ | CO | Nitrogen |
| $CF_3$—$CF_2$—$CF_2I$ | 1 ppm-10 ppm | | | | |
| | | 1 ppm-10 ppm | | | |
| | | | 1 ppm-10 ppm | | |
| | | | | 1 ppm-10 ppm | |
| | | | | | 1 ppm-10 ppm |
| | 1 ppm-10 ppm | 1 ppm-10 ppm | | | |
| | 1 ppm-10 ppm | | 1 ppm-10 ppm | | |
| | 1 ppm-10 ppm | | | 1 ppm-10 ppm | |
| | 1 ppm-10 ppm | | | | 1 ppm-10 ppm |
| | 1 ppm-10 ppm | 1 ppm-10 ppm | 1 ppm-10 ppm | | |
| | 1 ppm-10 ppm | 1 ppm-10 ppm | | 1 ppm-10 ppm | |
| | 1 ppm-10 ppm | 1 ppm-10 ppm | | | 1 ppm-10 ppm |
| | 1 ppm-10 ppm | | 1 ppm-10 ppm | 1 ppm-10 ppm | |
| | 1 ppm-10 ppm | | 1 ppm-10 ppm | | 1 ppm-10 ppm |
| | 1 ppm-10 ppm | | | 1 ppm-10 ppm | 1 ppm-10 ppm |
| | 1 ppm-10 ppm | 1 ppm-10 ppm | 1 ppm-10 ppm | 1 ppm-10 ppm | |
| | 1 ppm-10 ppm | 1 ppm-10 ppm | 1 ppm-10 ppm | | 1 ppm-10 ppm |
| | 1 ppm-10 ppm | | 1 ppm-10 ppm | 1 ppm-10 ppm | 1 ppm-10 ppm |
| | 1 ppm-10 ppm | 1 ppm-10 ppm | 1 ppm-10 ppm | 1 ppm-10 ppm | 1 ppm-10 ppm |
| | | 1 ppm-10 ppm | 1 ppm-10 ppm | | |
| | | 1 ppm-10 ppm | | 1 ppm-10 ppm | |
| | | 1 ppm-10 ppm | | | 1 ppm-10 ppm |
| | | 1 ppm-10 ppm | 1 ppm-10 ppm | 1 ppm-10 ppm | |
| | | 1 ppm-10 ppm | 1 ppm-10 ppm | | 1 ppm-10 ppm |
| | | 1 ppm-10 ppm | | 1 ppm-10 ppm | 1 ppm-10 ppm |
| | | 1 ppm-10 ppm | 1 ppm-10 ppm | 1 ppm-10 ppm | 1 ppm-10 ppm |
| | | | 1 ppm-10 ppm | 1 ppm-10 ppm | |
| | | | 1 ppm-10 ppm | | 1 ppm-10 ppm |
| | | | 1 ppm-10 ppm | 1 ppm-10 ppm | 1 ppm-10 ppm |
| | | | | 1 ppm-10 ppm | 1 ppm-10 ppm |

The compositions can be prepared by mixing the various constituents in their respective proportions. The compositions according to the invention may also be prepared according to the process described in application FR2001617 according to the process described in application FR2001619 or according to the process described in application FR2001620.

According to another aspect of the present invention, a storage device is provided. Said device comprises a sealed container within which the composition according to the invention as contained.

Preferably, the composition according to the invention is stored in a sealed container, in a liquid-gaseous state composed of a liquid phase and the gaseous phase. The storage of the composition in this liquid-gaseous state makes it possible to minimize the degradation of the composition over the storage time.

According to a preferred embodiment, the container withstands a test pressure, said test pressure being of between 10 and 100 bar, advantageously between 15 and 70 bar, preferably between 20 and 60 bar, in particular from 40 to 50 bar.

According to a preferred embodiment, the container is made of a material selected from carbon steel, stainless steel, manganese steel, chromium/molybdenum steel or an aluminum alloy.

According to a preferred embodiment, the container comprises an internal surface in contact with said composition, said internal surface being at least partially covered with a coating comprising zinc or with a resin of polyether or polyol type.

According to a preferred embodiment, at least 90% of said internal surface in contact with said composition is covered with said resin of polyether or polyol type, advantageously at least 95% of said internal surface in contact with said composition is covered with said resin of polyether or polyol type, preferably at least 98% of said internal surface in contact with said composition is covered with said resin of polyether or polyol type, in particular at least 99% of said internal surface in contact with said composition is covered with said resin of polyether or polyol type, more particularly the entire internal surface of the receptacle in contact with said composition is covered with said resin of polyether or polyol type.

The resin of polyether or polyol type can result from monomers comprising an oxirane or phenol functional group. Preferably, the resin of polyether or polyol type results from monomers comprising a siloxirane unit. In particular, the resin of polyether or polyol type results from monomers comprising a siloxirane unit of formula (III):

(III)

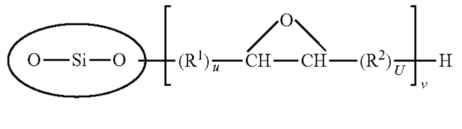

wherein $R^1$ and $R^2$ are, independently of one another and independently for each unit u and v, a group of the following types: $C_6$-$C_{18}$ aryl, $C_1$-$C_{20}$ alkyl, $C_3$-$C_{20}$ cycloalkyl, $C_3$-$C_{20}$ cycloalkenyl, $C_2$-$C_{20}$ alkenyl, carbonyl of formula $R^3$—C(O)—$R^4$, ester of formula $R^3$—C(O)—O—$R^4$, ether of formula $R^3$—O—$R^4$; an amine of formula $R^3$—N—$R^4$, it also being possible for $R^2$ to be an aldehyde group of formula $R^3$—C(O)—H; $R^3$ and $R^4$ being chosen, independently of one another, from a $C_6$-$C_{18}$ aryl, $C_1$-$C_{20}$ alkyl, $C_3$-$C_{20}$ cycloalkyl, $C_3$-$C_{20}$ cycloalkenyl or $C_2$-$C_{20}$ alkenyl group;

v is an integer from 1 to 30, advantageously from 1 to 20, preferably from 5 to 10; and u is independently, for $R^1$ and $R^2$, an integer from 1 to 30, advantageously from 1 to 20, preferably from 5 to 10.

According to another preferred embodiment, the resin of polyether or polyol type results from condensates of a compound A1 with a compound B1, the compound A1 being a substituted or unsubstituted phenol compound and the compound B1 being a compound of formula $R^5C(O)R^6$ wherein $R^5$ and $R^6$ are independently hydrogen, $C_1$-$C_{20}$ alkyl, $C_6$-$C_{20}$ aryl, $C_3$-$C_{20}$ cycloalkyl or $C_2$-$C_{20}$ alkenyl. The substituted phenol compound can be substituted by any one of the abovementioned substituents. Preferably, the compound A1 is an unsubstituted phenol.

Advantageously, the compound B1 is a compound of formula $R^5C(O)R^6$ wherein $R^5$ and $R^6$ are independently hydrogen, $C_1$-$C_{10}$ alkyl, $C_6$-$C_{10}$ aryl, $C_3$-$C_{10}$ cycloalkyl or $C_2$-$C_{10}$ alkenyl. Preferably, the compound B1 is a compound of formula $R^5C(O)R^6$ wherein $R^5$ and $R^6$ are independently hydrogen, $C_1$-$C_5$ alkyl, $C_6$-$C_{10}$ aryl, $C_3$-$C_6$ cycloalkyl or $C_2$-$C_5$ alkenyl. In particular, the compound B1 is a compound of formula $R^5C(O)R^6$ wherein $R^5$ and $R^6$ are hydrogen. Preferably, the compound A1 is phenol $C_6H_5OH$ and the compound B1 is formaldehyde.

According to another preferred embodiment, at least 90% of said internal surface in contact with said composition can be covered with a coating comprising zinc, advantageously at least 95% of said internal surface in contact with said composition can be covered with a coating comprising zinc, preferably at least 98% of said internal surface in contact with said composition can be covered with a coating comprising zinc, in particular at least 99% of said internal surface in contact with said composition can be covered with a coating comprising zinc. More particularly, the entire internal surface in contact with said composition contained in said receptacle can be covered with a coating comprising zinc.

Preferably, the coating comprises at least 50% by weight of zinc on the basis of the total weight of the coating, advantageously at least 70% by weight on the basis of the total weight of the coating, preferably at least 90% by weight of zinc on the basis of the total weight of the coating, more preferentially at least 95% by weight of zinc on the basis of the total weight of the coating, in particular at least 99% of zinc on the basis of the total weight of the coating, more particularly at least 99.9% of zinc on the basis of the total weight of the coating.

Alternatively, the coating can be an alloy comprising zinc, preferably less than 50% by weight of zinc, on the basis of the total weight of the coating. For example, the coating can be brass. Alternatively, the coating can comprise copper, advantageously at least 60% by weight of copper, on the basis of the total weight of the coating, preferably at least 70% by weight of copper, on the basis of the total weight of the coating, in particular at least 90% by weight of copper, on the basis of the total weight of the coating. Alternatively, the receptacle as described in the present patent application can also have an internal surface, preferably the entire internal surface in contact with said composition, covered with a coating comprising copper or brass in place of zinc.

According to another preferred embodiment, said internal surface of said container is covered with a thermal insulator comprising a polymer material having closed pores, the latter being formed from and/or containing a haloalkene of formula (III) $R_2C$═CRR' in which R is independently selected from the group consisting of Cl, F, H and $CF_3$ and R' is $(CR_2)_nY$, where Y is $CF_3$ and n is 0 or 1. Preferably, said haloalkene of formula (III) is selected from the group consisting of (E/Z)-1,1,1,4,4,4-hexafluoro-2-butene, (E/Z)-1-chloro-3,3,3-trifluoropropene and (Z/E)-1,3,3,3-tetrafluoropropene.

The invention claimed is:

1. A composition comprising at least 99.5% by weight of an iodofluorocarbon compound A and at most 0.5% by weight of at least one compound B chosen from water, HF, HI, $IF_5$, $I_2$, $O_2$, $CO_2$, CO and nitrogen or a mixture thereof; said iodofluorocarbon compound A being of formula (I) $(R^1)(R^2)C(I)(R^3)$ or of formula (II) $(R^1)(R^2)C$═$C(I)(R^3)$; wherein $R^1$, $R^2$ and $R^3$ are, independently of one another, selected from the group consisting of H, F, I, a $C_1$-$C_{10}$ alkyl radical optionally substituted with at least one fluorine or iodine atom, a $C_3$-$C_{10}$ cycloalkyl radical optionally substituted with at least one fluorine or iodine atom, a $C_2$-$C_{10}$ alkenyl radical optionally substituted with at least one fluorine or iodine atom, a $C_3$-$C_{10}$ cycloalkenyl radical optionally substituted with at least one fluorine or iodine atom, and a $C_6$-$C_{10}$ aryl radical optionally substituted with at least one fluorine or iodine atom; on condition that at least one of the substituents $R^1$, $R^2$ or $R^3$ is F or is a radical as defined above comprising at least one fluorine atom and on condition that the iodofluorocarbon compound A is not $CF_3I$, wherein said composition comprises at most 10 ppm of HI, at most 10 ppm of HF, at most 10 ppm of $IF_5$, and at most 10 ppm of L, each by weight based on the total weight of the composition.

2. The composition as claimed in claim 1, wherein the composition comprises at least 99.9% by weight of said compound A and at most 0.1% by weight of said at least one compound B.

3. The composition as claimed in claim 1, wherein the composition comprises at least 99.9% by weight of said compound A and at most 1000 ppm of water.

4. The composition as claimed in claim 1, wherein the composition comprises at least 99.9% by weight of said compound A and at most 1000 ppm of HI.

5. The composition as claimed in claim 1, wherein the composition comprises at least 99.9% by weight of said compound A and at most 1000 ppm of HF.

6. The composition as claimed in claim 1, wherein the composition comprises at least 99.9% by weight of said compound A and at most 1000 ppm of $IF_5$.

7. The composition as claimed in claim 1, wherein the composition comprises at least 99.9% by weight of said compound A and at most 1000 ppm of $I_2$.

8. The composition as claimed in claim 1, wherein the composition comprises at least 99.9% by weight of said compound A and at most 1000 ppm of $O_2$.

9. The composition as claimed in claim 1, wherein the composition comprises at least 99.9% by weight of said compound A and at most 1000 ppm of $CO_2$.

10. The composition as claimed in claim 1, wherein the composition comprises at least 99.9% by weight of said compound A and at most 1000 ppm of CO.

11. The composition as claimed in claim 1, wherein the composition 3 comprises at least 99.9% by weight of said compound A and at most 1000 ppm of nitrogen.

12. A compound as claimed in claim 1, wherein said compound A is of formula (I) or (II), wherein $R^1$, $R^2$ and $R^3$ are, independently of one another, selected from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; on condition that at least one of the substituents $R^1$, $R^2$ or $R^3$ is F or is a radical as defined here comprising at least one fluorine atom; and on condition that the iodofluorocarbon compound A is not $CF_3I$.

13. The composition as claimed in claim 1, wherein said compound A is of formula (I) or (II), wherein $R^1$, $R^2$ and $R^3$ are, independently of one another, selected from the group consisting of H, F or $Y^1$—[—$C(Y^2)(Y^3)$—$]_n$— wherein $Y^1$, $Y^2$, and $Y^3$ are, independently of one another and independently for each unit n, selected from the group consisting of H, I and F; and n is an integer from 1 to 5; on condition that at least one of the substituents $R^1$, $R^2$, $R^3$, $Y^1$, $Y^2$ or $Y^3$ is a fluorine atom and on condition that the iodofluorocarbon compound A is not $CF_3I$.

14. The composition as claimed in claim 1, wherein said compound A is selected from the group consisting of $CH_2FI$, $CHF_2I$, $CH_2F$—$CH_2I$, CHFI—$CH_3$, CFI═$CH_2$, cis-CHF═CHI, trans-CHF═CHI, $CHF_2$—$CH_2I$, $CF_2I$—$CH_3$, $CF_3$—$CH_2I$, $CF_2$═CHI, $CH_2F$—CHFI, cis-CFI═CHF, trans-CFI═CHF, $CHF_2$—CHFI, $CF_2I$—$CH_2F$, $CF_3$—CHFI, $CF_2$═CFI, $CHF_2$—$CF_2I$, $CF_2I$—$CF_3$, $CH_3$—CHF—$CH_2I$, $CH_3$—CFI—$CH_3$, $CH_3$—$CF_2$—$CH_2I$, $CH_2$═CF—$CH_2I$, cis-$CH_3$—CF═CHI, trans-$CH_3$—CF═CHI, $CH_3$—$CH_2$—CHFI, $CH_3$—CHI—$CH_2F$, $CH_2$═CH—CHFI, cis-$CH_3$—CI═CHF, trans-$CH_3$—CI═CHF, cis-$CH_3$—CH═CFI, trans-$CH_3$—CH═CFI, $CH_2F$—$CH_2$—$CH_2I$, cis-CHF═CH—$CH_2I$, trans-CHF═CH—$CH_2I$, $CH_2F$—CI═$CH_2$, cis-$CH_2F$—CH═CHI, trans-$CH_2F$—CH═CHI, $CH_3$—CHF—CHFI, $CH_3$—CFI—$CH_2F$, $CH_3$—$CF_2$—CHFI, $CH_2$═CF—CHFI, cis-$CH_3$—CF═CFI, trans-$CH_3$—CF═CFI, $CH_2F$—CHF—$CH_2I$, $CH_2F$—$CF_2$—$CH_2I$, cis-CHF═CF—$CH_2I$, trans-CHF═CF—$CH_2I$, cis-$CH_2F$—CF═CHI, trans-$CH_2F$—CF═CHI, $CH_3$—$CH_2$—$CF_2I$, $CH_3$—CHI—$CHF_2$, $CH_2$═CH—$CF_2I$, $CH_3$—CI═$CF_2$, $CH_2F$—$CH_2$—CHFI, $CH_2F$—CHI—$CH_2F$, cis-CHF═CH—CHFI, trans-CHF═CH—CHFI, cis-$CH_2F$—CI═CHF, trans-$CH_2F$—CI═CHF, cis-$CH_2F$—CH═CFI, trans-$CH_2F$—CH═CFI, $CHF_2$—$CH_2$—$CH_2I$, $CF_2$═CH—$CH_2I$, $CHF_2$—CI═$CH_2$, cis-$CHF_2$—CH═CHI, trans-$CHF_2$—CH═CHI, $CH_3$—CHF—$CF_2I$, $CH_3$—CFI—$CHF_2$, $CH_3$—$CF_2$—$CF_2I$, $CH_2$═CF—$CF_2I$, $CH_2F$—CHF—CHFI, $CH_2F$—CFI—$CH_2F$, $CH_2F$—$CF_2$—CHFI, cis-CHF═CF—CHFI, trans-CHF═CF—CHFI, cis-$CH_2F$—CF═CFI, trans-$CH_2F$—CF═CFI, $CHF_2$—CHF—$CH_2I$, $CHF_2$—$CF_2$—$CH_2I$, $CF_2$═CF—$CH_2I$, cis-$CHF_2$—CF═CHI, trans-$CHF_2$—CF═CHI, $CH_2F$—$CH_2$—$CF_2I$, $CH_2F$—CHI—$CHF_2$, cis-CHF═CH—$CF_2I$, trans-CHF═CH—$CF_2I$, $CH_2F$—CI═$CF_2$, $CHF_2$—$CH_2$—CHFI, $CF_2$═CH—CHFI, cis-$CHF_2$—CI═CHF, trans-$CHF_2$—CI═CHF, cis-$CHF_2$—CH═CFI, trans-$CHF_2$—CH═CFI, $CF_3$—$CH_2$—$CH_2I$, $CF_3$—CHI—$CH_3$, $CF_3$—CI═$CH_2$, cis-$CF_3$—CH═CHI, trans-$CF_3$—CH═CHI, $CH_2F$—CHF—$CF_2I$, $CH_2F$—CFI—$CHF_2$, $CH_2F$—$CF_2$—$CF_2I$, cis-CHF═CF—$CF_2I$, trans-CHF═CF—$CF_2I$, $CHF_2$—CHF—CHFI, $CHF_2$—$CF_2$—CHFI, $CF_2$═CF—CHFI, cis-$CHF_2$—CF═CFI, trans-$CHF_2$—CF═CFI, $CF_3$—CHF—$CH_2I$, $CF_3$—CFI—$CH_3$, $CF_3$—$CF_2$—$CH_2I$, cis-$CF_3$—CF═CHI, trans-$CF_3$—CF═CHI, $CHF_2$—$CH_2$—$CF_2I$, $CHF_2$—CHI—$CHF_2$, $CF_2$═CH—$CF_2I$, $CHF_2$—CI═$CF_2$, $CF_3$—$CH_2$—CHFI, $CF_3$—CHI—$CH_2F$, cis-$CF_3$—CI═CHF, trans-$CF_3$—CI═CHF, cis-$CF_3$—CH═CFI, trans-$CF_3$—CH═CFI, $CHF_2$—CHF—$CF_2I$, $CHF_2$—CFI—$CHF_2$, $CHF_2$—$CF_2$—$CF_2I$, $CF_2$═CF—$CF_2I$, $CF_3$—CHF—CHFI, $CF_3$—CFI—$CH_2F$, $CF_3$—$CF_2$—CHFI, cis-$CF_3$—CF═CFI, trans-$CF_3$—CF═CFI, $CF_3$—$CH_2$—$CF_2I$, $CF_3$—CHI—

$CHF_2$, $CF_3$—CHI—$CF_3$, $CF_3$—CI═$CF_2$, $CF_3$—CHF—$CF_2I$, $CF_3$—CFI—$CHF_2$, $CF_3$—CFI—$CF_3$, and $CF_3$—$CF_2$—$CF_2I$.

15. The composition as claimed in claim 1, wherein said compound A is selected from the group consisting of $CHF_2I$, $CHF_2$—$CH_2I$, $CF_2I$—$CH_3$, $CF_3$—$CH_2I$, $CF_2$═CHI, $CHF_2$—CHFI, $CF_2I$—$CH_2F$, $CF_3$—CHFI, $CF_2$═CFI, $CHF_2$—$CF_2I$, $CF_2I$—$CF_3$, $CF_3$—$CH_2$—$CH_2I$, $CF_3$—CHI—$CH_3$, $CF_3$—CI═$CH_2$, cis-$CF_3$—CH═CHI, trans-$CF_3$—CH═CHI, $CF_3$—CHF—$CH_2I$, $CF_3$—CFI—$CH_3$, $CF_3$—$CF_2$—$CH_2I$, cis-$CF_3$—CF═CHI, trans-$CF_3$—CF═CHI, $CF_3$—$CH_2$—CHFI, $CF_3$—CHI—$CH_2F$, cis-$CF_3$—CI═CHF, trans-$CF_3$—CI═CHF, cis-$CF_3$—CH═CFI, trans-$CF_3$—CH═CFI, $CF_3$—CHF—CHFI, $CF_3$—CFI—$CH_2F$, $CF_3$—$CF_2$—CHFI, cis-$CF_3$—CF═CFI, trans-$CF_3$—CF═CFI, $CF_3$—CHF—$CF_2I$, $CF_3$—CFI—$CHF_2$, $CF_3$—CFI—$CF_3$, and $CF_3$—$CF_2$—$CF_2I$.

16. The composition as claimed in claim 1, wherein said compound A is selected from the group consisting of $CHFI_2$, $CF_2I_2$, $CFI_2$—$CH_3$, $CH_2F$—$CHI_2$, CHFI—$CH_2I$, $CHF_2$—$CHI_2$, $CF_2I$—$CH_2I$, $CFI_2$—$CH_2F$, CHFI—CHFI, $CF_3$—$CHI_2$, $CHF_2$—$CFI_2$, $CF_2I$—CHFI, $CF_3$—$CFI_2$, $CF_2I$—$CF_2I$, $CFI_2$—$CH_2$—$CH_3$, $CH_2F$—$CI_2$—$CH_3$, $CH_2F$—$CH_2$—$CHI_2$, CHFI—CHI—$CH_3$, CHFI—$CH_2$—$CH_2I$, $CH_2F$—CHI—$CH_2I$, $CHI_2$—CHF—$CH_3$, $CH_2I$—CFI—$CH_3$, $CH_2I$—CHF—$CH_2I$, $CFI_2$—$CH_2$—$CH_2F$, $CH_2F$—$CI_2$—$CH_2F$, CHFI—CHI—$CH_2F$, CHFI—$CH_2$—CHFI, $CHF_2$—$CI_2$—$CH_3$, $CHF_2$—$CH_2$—$CHI_2$, $CF_2I$—CHI—$CH_3$, $CF_2I$—$CH_2$—$CH_2I$, $CHF_2$—CHI—$CH_2I$, $CFI_2$—CHF—$CH_3$, $CH_2F$—CHF—$CHI_2$, CHFI—CFI—$CH_3$, CHFI—CHF—$CH_2I$, $CH_2F$—CFI—$CH_2I$, $CHI_2$—$CF_2$—$CH_3$, $CH_2I$—$CF_2$—$CH_2I$, $CHF_2$—$CI_2$—$CH_2F$, $CHF_2$—$CH_2$—$CFI_2$, $CF_2I$—CHI—$CH_2F$, $CF_2I$—$CH_2$—CHFI, $CHF_2$—CHI—CHFI, $CF_3$—$CI_2$—$CH_3$, $CF_3$—$CH_2$—$CHI_2$, $CF_3$—CHI—$CH_2I$, $CFI_2$—CHF—$CH_2F$, CHFI—CFI—$CH_2F$, CHFI—CHF—CHFI, $CHF_2$—CHF—$CHI_2$, $CF_2I$—CFI—$CH_3$, $CF_2I$—CHF—$CH_2I$, $CHF_2$—CFI—$CH_2I$, $CFI_2$—$CF_2$—$CH_3$, $CH_2F$—$CF_2$—$CHI_2$, CHFI—$CF_2$—$CH_2I$, $CHF_2$—$CI_2$—$CHF_2$, $CF_2I$—CHI—$CHF_2$, $CF_2I$—$CH_2$—$CF_2I$, $CF_3$—$CI_2$—$CH_2F$, $CF_3$—$CH_2$—$CFI_2$, $CF_3$—CHI—CHFI, $CHF_2$—CHF—$CFI_2$, $CF_2I$—CFI—$CH_2F$, $CF_2I$—CHF—CHFI, $CHF_2$—CFI—CHFI, $CF_3$—CHF—$CHI_2$, $CF_3$—CFI—$CH_2I$, $CFI_2$—$CF_2$—$CH_2F$, CHFI—$CF_2$—CHFI, $CHF_2$—$CF_2$—$CHI_2$, $CF_2I$—$CF_2$—$CH_2I$, $CF_3$—$CI_2$—$CHF_2$, $CF_3$—CHI—$CF_2I$, $CF_2I$—CFI—$CHF_2$, $CF_2I$—CHF—$CF_2I$, $CF_3$—CHF—$CFI_2$, $CF_3$—CFI—CHFI, $CHF_2$—$CF_2$—$CFI_2$, $CF_2I$—$CF_2$—CHFI, $CF_3$—$CF_2$—$CHI_2$, $CF_3$—$CI_2$—$CF_3$, $CF_3$—CFI—$CF_2I$, $CF_2I$—$CF_2$—$CF_2I$, and $CF_3$—$CF_2$—$CFI_2$.

17. The composition as claimed in claim 1, wherein said compound A is selected from the group consisting of $CF_2I_2$, $CHF_2$—$CHI_2$, $CF_2I$—$CH_2I$, $CF_3$—$CHI_2$, $CF_3$—$CFI_2$, $CFI_2$—CHF—$CH_3$, $CH_2F$—CHF—$CHI_2$, CHFI—CFI—$CH_3$, CHFI—CHF—$CH_2I$, $CH_2F$—CFI—$CH_2I$, $CF_3$—$CI_2$—$CH_3$, $CF_3$—$CH_2$—$CHI_2$, $CF_3$—CHI—$CH_2I$, $CF_3$—$CI_2$—$CH_2F$, $CF_3$—$CH_2$—$CFI_2$, $CF_3$—CHI—CHFI, $CF_3$—CHF—$CHI_2$, $CF_3$—CFI—$CH_2I$, $CF_3$—$CI_2$—$CHF_2$, $CF_3$—CHI—$CF_2I$, $CF_3$—CHF—$CFI_2$, $CF_3$—CFI—CHFI, $CF_3$—$CI_2$—$CF_3$, $CF_3$—CFI—$CF_2I$, and $CF_2I$—CHFI.

18. A precision cleaning agent comprising the composition as claimed in claim 1.

* * * * *